(12) United States Patent
Quint et al.

(10) Patent No.: US 11,796,477 B2
(45) Date of Patent: Oct. 24, 2023

(54) RELIABILITY INDICATING METHOD FOR AN ELECTROCHEMILUMINESCENCE METHOD FOR DETECTING AN ANALYTE IN A LIQUID SAMPLE

(71) Applicant: Roche Diagnostics Operations, Inc., Indianapolis, IN (US)

(72) Inventors: Stefan Quint, Munich (DE); Klaus Bauer-Espindola, Mannheim (DE)

(73) Assignee: ROCHE DIAGNOSTICS OPERATIONS, INC., Indianapolis, IN (US)

(*) Notice: Subject to any disclaimer, the term of this patent is extended or adjusted under 35 U.S.C. 154(b) by 812 days.

(21) Appl. No.: 16/044,897

(22) Filed: Jul. 25, 2018

(65) Prior Publication Data

US 2018/0348140 A1    Dec. 6, 2018

Related U.S. Application Data

(63) Continuation of application No. PCT/EP2017/051868, filed on Jan. 27, 2017.

(30) Foreign Application Priority Data

Jan. 29, 2016  (EP) .................................. 16153257
Mar. 1, 2016   (EP) .................................. 16158014

(51) Int. Cl.
*G01N 21/66* (2006.01)
*G01N 35/00* (2006.01)
(Continued)

(52) U.S. Cl.
CPC ......... *G01N 21/66* (2013.01); *G01N 27/3277* (2013.01); *G01N 27/4163* (2013.01);
(Continued)

(58) Field of Classification Search
CPC .... G01N 21/66; G01N 21/76; G01N 27/4163; G01N 35/00594–00712; G01N 2035/00633–00683
See application file for complete search history.

(56) References Cited

U.S. PATENT DOCUMENTS 5,238,808 A    8/1993  Bard et al.
5,667,651 A    9/1997  Bryan
(Continued)

FOREIGN PATENT DOCUMENTS

CN    103076572 A    5/2013
CN    103604921 A    2/2014
(Continued)

OTHER PUBLICATIONS

"electrogenerated chemiluminescence (ECL)," Iupac. Compendium of Chemical Terminology, 2nd ed. (the "Gold Book"). Compiled by A. D. McNaught and A. Wilkinson. Blackwell Scientific Publications, Oxford (1997). Last revised: Feb. 24, 2014 doi: 10.1351/goldbook.E01966 (Year: 2014).*
(Continued)

*Primary Examiner* — Jennifer Wecker
*Assistant Examiner* — Michelle Adams
(74) *Attorney, Agent, or Firm* — Woodard, Emhardt, Henry, Reeves & Wagner, LLP

(57) ABSTRACT

Described is an electrochemiluminescence method of detecting an analyte in a liquid sample using a measuring cell having a working electrode for detecting the analyte using an electrochemiluminescence measurement cycle, involving
a. carrying out the measurement cycle in a calibration process using a liquid sample without analyte and performing a first electrochemical impedance spectroscopy, EIS, at a given point of the measurement cycle, the first EIS being performed using the working electrode,
(Continued)

b. carrying out the measurement cycle in an analysis process using the liquid sample containing the analyte and performing a second EIS at the given point of the measurement cycle, the second EIS being performed using the working electrode, c. comparing the result of the first EIS and the second EIS, providing an indication indicating if the comparison results show a deviation between the first EIS and the second EIS exceed a predefined threshold.

17 Claims, 23 Drawing Sheets

(51) Int. Cl.
    *G01N 27/327* (2006.01)
    *G01N 27/416* (2006.01)
    *G01N 35/10* (2006.01)

(52) U.S. Cl.
    CPC . *G01N 35/00623* (2013.01); *G01N 35/00722* (2013.01); *G01N 35/1004* (2013.01); *G01N 2035/00891* (2013.01)

(56) References Cited

U.S. PATENT DOCUMENTS

| | | |
|---|---|---|
| 6,599,473 B1 | 7/2003 | Egger et al. |
| 2008/0193965 A1 | 8/2008 | Zeng et al. |
| 2009/0000958 A1 | 1/2009 | Tayler et al. |
| 2010/0121578 A1 | 5/2010 | Davis |

FOREIGN PATENT DOCUMENTS

| | | |
|---|---|---|
| CN | 103940808 B | 7/2014 |
| DE | 102011005966 A1 | 9/2012 |
| WO | 1986/002734 A1 | 5/1986 |
| WO | 1990/011511 A1 | 10/1990 |
| WO | 1999/039206 A1 | 8/1999 |
| WO | 2004/011931 A2 | 2/2004 |
| WO | 2004/061418 A2 | 7/2004 |
| WO | 2005/001462 A1 | 1/2005 |
| WO | 2008/084114 A1 | 7/2008 |
| WO | 2009/054474 A1 | 4/2009 |
| WO | 2010/014622 A2 | 2/2010 |
| WO | 2014/202298 A1 | 12/2014 |
| WO | 2015/094576 A2 | 8/2015 |

OTHER PUBLICATIONS

International Search Report dated Mar. 10, 2017, in Application No. PCT/EP2017/051868, 4 pp.

Lee, Won-Yong, Tris (2,2'-bipyridyl)ruthenium(II) Electrogenerated Chemiluminescence in Analytical Science, Mikrochimica Acta, 1997, pp. 19-39, vol. 127.

* cited by examiner

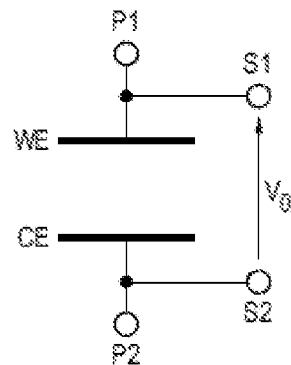
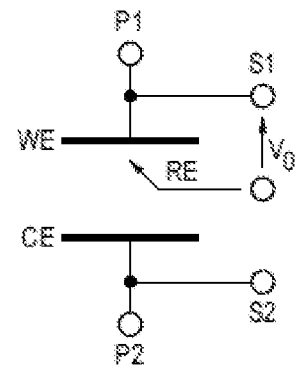
Fig. 4a  Fig. 4b
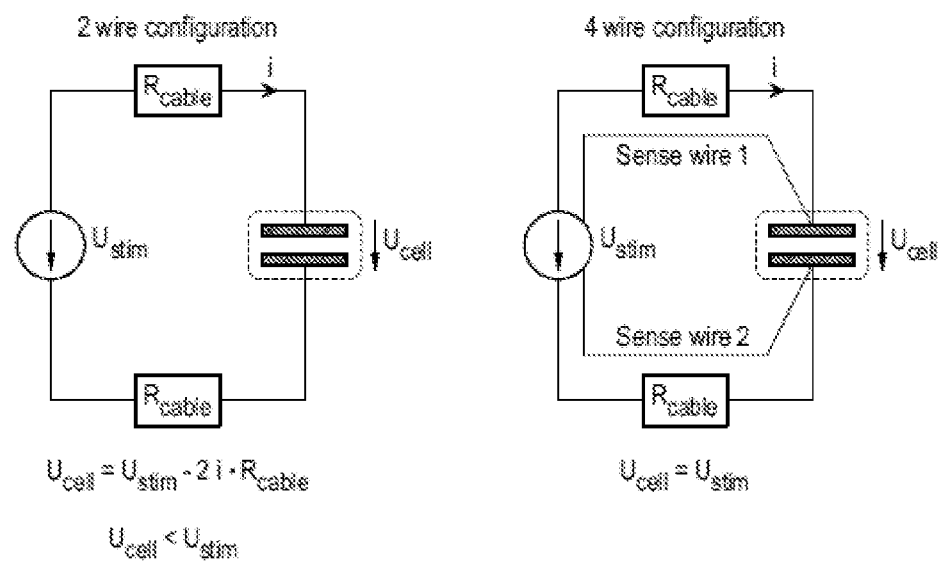
Fig. 4c

| a | b | c | d | Issue | Actions |
|---|---|---|---|---|---|
| OK | OK | OK | NOK (P+A)* | CIS irregular condition | i. Clean CIS cup & sipper nozzle<br>ii. Change CIS lot |
| OK | OK | OK | NOK (only A) | Anomalous Incubate | i. Set flag<br>ii. Check sample<br>iii. Rerun determination |
| NOK (P+A) | NOK (P+A) | NOK (P+A) | NOK (P+A) | CoS irregular condition | i. Clean CoS cup & sipper nozzle<br>ii. Change CoS lot |
| NOK (P+A) | NOK (P+A) | NOK (P+A) | NOK (P+A) | MC irregular condition | i. Perform LFC<br>ii. Change MC |
| OK | NOK | OK | OK | Anomalous Incubate | i. Set flag<br>ii. Clean sipper nozzle & check adjustment<br>iii. Rerun determination |

Fig. 5

RELIABILITY INDICATING METHOD FOR AN ELECTROCHEMILUMINESCENCE METHOD FOR DETECTING AN ANALYTE IN A LIQUID SAMPLE

CROSS REFERENCE TO RELATED APPLICATIONS

This application is a continuation of International Application No. PCT/EP2017/051868 filed Jan. 27, 2017, which claims priority to European Application No. 16153257.7 filed Jan. 29, 2016, and European Application No. 16158014.7 filed Mar. 1, 2016, all of which are hereby incorporated by reference in their entirety.

FIELD OF INVENTION

The invention relates to an electrochemiluminescence method of detecting an analyte in a liquid sample and an apparatus for detecting an analyte in a liquid sample, as well as a computer program product.

BACKGROUND AND RELATED ART

Electrochemiluminescent (ECL) assay techniques are well known for the detection and quantitation of analytes of interest in biochemical and biological substances. Generally, methods and systems which are capable of measuring trace amounts of microorganisms, pharmaceuticals, hormones, viruses, antibodies, nucleic acids and other proteins are of great value to researchers and clinicians.

ECL assay techniques provide a sensitive and precise measurement of the presence and concentration of an analyte of interest. In such techniques, the incubated sample is exposed to a potentiostatically or galvanostatically controlled working electrode in order to trigger luminescence. In the proper chemical environment, such electrochemiluminescence is triggered by a voltage or current impressed on the working electrode at a particular time and in a particular manner. The light produced by the label is measured and indicates the presence or quantity of the analyte. For a fuller description of such ECL techniques, reference is made to e.g. U.S. Pat. No. 5,238,808, and WO86/02734.

An electrochemiluminescence method of detecting an analyte in a liquid sample, where protein coated magnetic microparticles are stirred within a receptacle to prevent them from deposition at the bottom and aggregation with each other, is described in WO 2014/202298 A1 together with a suitable analysis system. WO 90/11511 discloses a method and an apparatus for conducting electrochemiluminescent measurements using a voltage waveform with a decreasing scan rate applied at a voltammetric working electrode to improve the precision and accuracy of measurements. In WO 99/39206, a method for analyzing a test sample by means of an electro-chemiluminsecence bond reaction test is described, wherein a complex containing a chemoluminescence marker, which is characteristic for the analysis, is formed through a biochemical bond reaction and bonded to a magnetic microparticle during a reaction sequence. In "Tris (2,2'-bipyridyl)ruthenium(II) Electrogenerated Chemiluminescence in Analytical Science", Microchim. Acta 127, 19-39, W.-Y. Lee describes how tris (2,2'-bipyridyl)ruthenium(II) electrogenerated chemiluminescence can be used as a detection method for the determination of oxalate and a variety of amine-containing analytes without derivatization in flowing streams such as flow injection and HPLC.

U.S. Pat. No. 6,599,473 B1 discloses an electrochemiluminescence binding reaction analysis (ECL-BBA).

In accordance with ECL-BBA a detectable complex is produced, whose concentration constitutes a measure of the analytic result sought. A marking substance (label) capable of effecting an ECL-reaction is coupled to a binding reagent specific for the analyte, e.g. an antibody. The species comprising the marking substance and the binding reagent is designated as a label conjugate.

When such a substance is subjected to a suitable electrical potential on a voltammetric working electrode, it emits light which can be measured photometrically. A second electrochemically active substance, designated as a co-reactant, normally contributes to this reaction. In practice, primarily a ruthenium complex (ruthenium-tris [bipyridyl]) is used as ECL-label in combination with tripropylamine (TPA) as co-reactant. The two electrochemically active substances are both oxidized upon voltage application to the electrode. Subsequent loss of a proton will turn the TPA into a strongly reducing species. The subsequent redox reaction brings the ECL-label into an excited state from which it returns to the ground state with the emission of a photon. The ECL-label reaction is preferably a circular reaction so that a single label molecule emits a plurality of photons after application of a voltage to the electrode.

The ECL-marked complex molecules characteristic for the analysis are fixed to magnetic microparticles (beads). In practice, magnetized polystyrene beads having a diameter of typically 2 to 3 micrometers are used. Fixing is effected by means of a pair of specific biochemical binding partners. The pair streptavidin biotin has turned out to be particularly advantageous. The beads are streptavidine-coated, to which a biotinylated antibody will bind.

The beads with the bound marked complex are introduced into the measuring cell of a measuring apparatus. The cell is equipped with electrodes which are necessary for generating the electrical field required for triggering the ECL-reaction. The beads are drawn onto the surface of the working electrode in the magnetic field of a magnet disposed below the working electrode. Since this typically occurs in flow-through cells with continuously flowing sample fluids, the magnetic deposition of the beads is designated as "capturing". An electric potential required for triggering the ECL-reaction is then applied to the working electrode and the resulting luminescence light is measured using a suitable optical detector. The intensity of the luminescence light is a measure for the concentration of the number of labeled antibodies coupled to the beads on the surface of the working electrode which, in turn, is a measure of the concentration of the analyte in the sample. A calibration allows calculation of the sought concentration from the measured luminescence signal.

SUMMARY OF THE INVENTION

In accordance with embodiments of the invention, an electrochemiluminescence method of detecting an analyte in a liquid sample using a measuring cell is provided. The measuring cell comprises a working electrode for detecting the analyte using an electrochemiluminescence measurement cycle. The method comprises a. carrying out the measurement cycle in a calibration process using a liquid sample void of the analyte and performing a first electrochemical impedance spectroscopy, EIS, at a given point of the measurement cycle, the first EIS being performed using the working electrode, b. carrying out the measurement cycle in an analysis process using the liquid sample containing the analyte and performing a second EIS at the given point of the measurement cycle, the second EIS being performed using the working electrode, c. comparing the result of the first EIS and the second EIS, d. providing an indication of a measurement state indicating if the comparison results that a deviation between the first EIS and the second EIS is exceeding a predefined threshold.

An 'analyte' as understood herein is a component of the liquid sample to be analyzed, e.g. molecules of various sizes, proteins, metabolites and the like.

A 'liquid sample' as understood herein encompasses a biological sample such as any kind of tissue or body fluid having been derived from a human or any other organism. In particular, a biological sample can be a blood-, serum-, plasma-, urine-, cerebral-spinal fluid-, or saliva-sample or any derivatives thereof.

The term 'luminescence' as understood herein encompasses any kind of luminescence such as radiation-induced luminescence, chemiluminescence and electrochemiluminescence, in particular ECL-BBA.

The term 'luminescence immunoassay' as understood herein encompasses any immunoassay that produces an optical signal, i.e. a luminescence signal that indicates the presence of a particular analyte in a liquid sample.

A 'measurement cycle' as understood herein encompasses the individual steps that are required in order to perform the electrochemiluminescence detection of the analyte in the liquid sample.

A 'given point of the measurement cycle' may be a given point in time for example after having started the measurement cycle. In this case, the given point may be a certain duration in time, measured either directly from the starting point of the cycle or after starting or completion of a certain step of the measurement cycle. A step of a measurement cycle is for example the provision of the liquid sample, the capturing of the microparticles, the washing of the measuring cell, the performing of the ECL measurement or the performing of the cleaning of the measuring cell. A given point may also be a well-defined certain instance of the measurement cycle, like for example said starting of one of the mentioned steps.

Even though only a working electrode is mentioned, the skilled person will understand that this also encompasses the presence of a counter electrode. Further, the skilled person will understand that this also encompasses a four electrode measurement with the $4^{th}$ electrode being used for compensation purposes.

The electrochemical impedance spectroscopy (EIS) result could be selected from the group consisting of admittance, impedance, real part, imaginary part or phase which is convertible into each other.

Electrochemical impedance spectroscopy (EIS) is a method that measures the dielectric properties of a medium, expressed by the impedance, as a function of frequency. The impedance Z of any circuit is the ratio between the voltage time-function $V(t)=V_0 \sin(\omega t)$ and the resulting current time response function $I(t)=I_0 \sin(\omega t+\varphi)$:

$$Z = \frac{V(t)}{I(t)} Z = \frac{V(t)}{I(t)} = \frac{V_0 \sin(\omega t)}{I_0 \sin(\omega t + \varphi)} = \frac{V_0 \sin(\omega t)}{I_0 \sin(\omega t + \varphi)}$$

Here $V_0$ and $I_0$ are the maximum voltage and current signals, w is the radial frequency, t the time and $\varphi$ is the phase shift. In general the impedance is determined at different frequencies to give an impedance spectrum $Z(\omega)$. The function Z can be represented by a complex number with the modulus $|Z|$, the phase shift $\varphi$, the real part $Z'$ and the imaginary part $Z''$. With $j=\sqrt{-1}\sqrt{-1}$ it can be written:

$$Z(\omega) = Z'(\omega) + jZ''(\omega) Z(\omega) = Z'(\omega) + jZ''(\omega)$$

$$\tan(\varphi) = -\frac{Z''(\omega)}{Z'(\omega)}$$

$$|Z| = \sqrt{(Z')^2 + (Z'')^2} \tan(\varphi) = -\frac{Z''(\omega)}{Z'(\omega)}$$

$$|Z| = \sqrt{(Z')^2 + (Z'')^2}$$

The real part of the impedance is related to all ohmic properties of the sample. The imaginary part describes mainly the capacitive behavior of the double layer capacitance which is formed at the Helmholtz layer very close to the electrode surface. The cell geometry and the geometry of the electrodes have a significant influence on the impedance. Any changes of the electrode surface have an influence on the double layer capacitance of an electrode. Therefore, electrochemical impedance spectroscopy is a powerful tool in order to evaluate the electrode surface in dependency of electrochemical reactions, adsorption effects, roughness or electrode fouling. EIS, therefore, is a powerful tool for quality control within a process.

Often the admittance is used as an alternative to the impedance. The admittance of a circuit is related to the impedance by the simple equation $$|Y| = \frac{1}{|Z|} |Y| = \frac{1}{|Z|}.$$

It is represented by the following equations:

$$Y(\omega) = Y'(\omega) + jY''(\omega) Z(\omega) = Y'(\omega) + jY''(\omega)$$

$$\tan(\varphi) = -\frac{Y''(\omega)}{Y'(\omega)}$$

$$|Y| = \sqrt{(Y')^2 + (Y'')^2} \tan(\varphi) = -\frac{Y''(\omega)}{Y'(\omega)}$$

$$|Y| = \sqrt{(Y')^2 + (Y'')^2}$$

When analyzing the Z or Y spectra Bode and Nyquist plots are most commonly used for representation. In the Bode plot log $|Z|$ and $\phi$ are plotted as a function of log $\omega/2\pi$, where in the Nyquist plot $-Z'$ is plotted versus $Z''$.

Embodiments of the invention may have the advantage that it is possible in situ, i.e. during the measurement cycle without interruption of the measurement cycle, to determine if the ECL measurement is reliable or not. For example, the measurement state may indicate a failure of the measurement cycle or a success of the measurement cycle. Failure means that the ECL measurement result is not trustworthy and success means that the ECL measurement result is reliable. Thus, embodiments may provide for a tool for judgment of the ECL measurement without interrupting or disturbing the measurement. For example, this may allow identifying irregular conditions within system reagents or components such as the co-reactant solution, the cleaning solution and the measuring cell.

Herein, the term 'co-reactant solution' (=CoS) is to be considered as a synonym for the reagent required as the ECL co-reactant. For example, 'co-reactant solution' may comprise Tripropylamine (TPA). A composition suitable as co-reactant solution (CoS) comprises for example 180 mM TPA, 300 mM Phosphate, 0.1% detergent (e.g. polidocanol), pH of 6.8.

Further, the term 'cleaning solution' (=CIS) is to be considered as a synonym for a measuring cell cleaning solution that is used to clean the cell after having performed the ECL measurement. For example, 'cleaning solution' may comprise Potassium Hydroxide.

A composition suitable as cleaning solution (CIS) comprises for example 176 mM KOH and 1% detergent (e.g. polidocanol).

In accordance with an embodiment of the invention, the measuring cell is part of a measurement apparatus which comprises a control unit, the indication being provided to the control unit, wherein in case the indication indicates that the comparison resulted that a deviation between the first EIS and the second EIS is exceeding the predefined threshold, the method further comprises controlling by the control unit the apparatus to:
  select a countermeasure regarding the measurement failure,
  initiate the countermeasure,
  repeat steps b., c. and d.

A 'countermeasure' is to be understood as any action that either controls the apparatus to correct for the failure of the measurement cycle or that provides an information to a user of the apparatus about the measurement failure or the EIS measurements.

For example, the countermeasure corrects for the measurement failure. After completion of the correction the repetition of said steps b., c. and d. may be automatically performed.

In a further example, the measurement apparatus further comprises a display unit, the countermeasure comprising displaying the measurement state on the display unit. In accordance with an embodiment, the displaying may only be performed in case the comparison resulted that a deviation between the first EIS and the second EIS is exceeding the predefined threshold.

In accordance with an embodiment of the invention, the measurement cycle comprises any one of the following:
  a first phase for conditioning of the working electrode without the liquid sample,
  a second phase for provision of the liquid sample to the measuring cell and capturing of magnetic microparticles, said liquid sample comprising a marking substance capable of effecting an electrochemiluminescence reaction measured with the electrochemiluminescence measurement, said complex further being bound to the magnetic microparticles, wherein in case the liquid sample contains the analyte, the analyte is being contained in the liquid sample as a complex, said complex comprising the marking substance, said capturing comprising attracting the microparticles by a magnetic field thereby depositing the microparticles on the surface of said working electrode,
  a third phase for washing of the measuring cell after the capturing and before the electrochemiluminescence measurement, said third phase being adapted to remove unbound complexes and non-deposited microparticles from the measuring cell,
  a fourth phase for performing the electrochemiluminescence measurement on the sample,
  a fifth phase for cleaning of the measuring cell with the working electrode with a cleaning solution, the given point being any one of the following:
  a first point during the first phase,
  a second point during second phase, wherein in case the third phase is not present, this second point may be at the very end of the second phase just before starting of the fourth phase,
  a third point during the third phase, preferably at the very end of the third phase,
  a fourth point during the fourth phase,
  a fifth point after the fifth phase and before the first phase in the subsequent run of the measurement cycle.

Preferably, any EIS measurement at any one of the given points may be performed at an instance with absence of movement of the liquids contained in the measuring cell. This may increase the accuracy of the method.

Regarding the third point it has to be noted, that preferably this third point may be selected such that the attraction of the microparticles is completed. This may provide for a reproducible state in which the EIS measurements are performed.

The appropriate selection of one or multiple ones of the above mentioned points may have the benefit that the above mentioned erroneous system reagents or components may be identified with a high selectivity. Thus, an error may be directly and unambiguously assigned to a defect of a certain system reagent or component. Said mentioned points may either be discrete individual points or they may form part of points obtained from a continuous EIS measurement. The EIS measurement may also be continuous for a certain phase, while for another phase the EIS measurement may only be performed for a discrete given point.

In accordance with an embodiment of the invention, the conditioning, the capturing, the optional washing, the electrochemiluminescence measurement and the cleaning are comprising applying potential pulses to the working electrode, the pulses being applied relative to a DC polarization potential measured relative to a reference electrode of the measuring cell, the performing of the EIS comprising applying an AC potential on the DC potential.

Thus, the standard DC potential required to perform the ECL measurement may be used as a basic potential such that the ECL measurement results are obtained with high precision and quality. On top of that DC potential the AC potential required for the EIS may be modulated such that it does not negatively affect the ECL measurement. For example, the DC potential during the ECL measurement cycle can be between −1.5 V and +3.0 V, preferably between −1.2 V to +1.2 V, more preferably 0 V.

For example, the AC potential for performing of the EIS is applied using a potentiostat with a Frequency Response Analysis (FRA) module. The EIS may then be performed using a potentiostatic single potential measurement.

The FRA-hardware may comprise a digital signal generator (DSG), a signal conditioning unit (SCU) and a fast analog to digital converter with two channels (ADC). The DSG may comprise a digital memory which is loaded with the digital representation of the applied signal and a digital to analog converter. A multiplying digital to analog converter may control the signal amplitude. This architecture may ensure accurate signal generation. The time dependent potential and current signals from the potentiostat are filtered and amplified by the SCU and recorded by means of the ADC. The acquired signals are stored in the digital memory on the ADC board. This digital memory allows time domain averaging of repetitive measurements at the same given measurement point.

For example, the AC potential has an amplitude of at least 1 mV and at most 100 mV peak to peak, preferably of at least 3 mV and at most 80 mV peak to peak, more preferably of at least 5 mV and at most 50 mV peak to peak. Further, the AC potential may have a frequency of at least 10 Hz and at most 100 kHz, preferably of at least 20 Hz and at most 50 kHz, more preferably of at least 30 Hz and at most 10 kHz.

It has to be noted that in an embodiment EIS measurements may be performed more than one time for the given point. From the EIS measurements made for said given point an average value may be calculated. This may further improve the accuracy of the method. It is understood by the skilled person that of course for a certain point in time only a single EIS measurement can be performed. Further EIS measurements for "the same" given point are thus to be understood as measurements successive in time and immediately before, at and after the given point in time. Thus, multiple EIS measurements may be performed within a limited and predefined time frame including the given time point.

The working electrode may be selected from the group comprising gold, platinum, glassy-carbon, iridium and boron doped diamond. The reference electrode may be selected from the group comprising silver/silver chloride, saturated calomel, mercury/mercury (mercurous) oxide, mercury/mercury sulfate, copper/copper sulfate electrode. As an alternative to the reference electrode for the EIS measurement a "pseudo reference electrode" may be used which is preferably selected from the group comprising silver, platinum, gold and stainless steel.

In a further embodiment according to the present invention the EIS measurement is performed in a 4-wire sensing method. The 4-wire sensing method compensates the iR drop at the working electrode and at the counter electrode by 2 additional electrodes (sense wire 1 and sense wire 2) for the EIS measurement (iR compensation). These 2 additional electrodes for the EIS measurement in a 4-wire sensing method are preferably selected from the group comprising silver, platinum, gold and stainless steel, respectively. In a further embodiment the AC potential for performing the EIS is applied using a potentiostat with a Frequency Response Analysis (FRA) module in 4-wire sensing method.

In accordance with an embodiment of the invention, the result of the first EIS and the second EIS is each comprising a respective response signal indicating an admittance and a phase, the predefined threshold being respectively defined for the admittance and the phase, the comparison of the result of the first EIS and second EIS comprising a comparison of the respective admittances and a comparison of the respective phases, the measurement state indicating if both comparisons result that a deviation between the first EIS and the second EIS is exceeding the threshold respectively predefined for the admittance and the phase.

Since within a single measurement the result of an EIS always comprises two type of information, namely phase and admittance, the usage of both information in combination as a criterion for determining the measurement state may increase the reliability of the method.

In accordance with an embodiment of the invention, the indication of a measurement state being positive in case the comparison results that a deviation between the compared EIS is within the predefined threshold and an the indication of a measurement state being negative in case the comparison results that a deviation between compared EIS is outside the predefined threshold, the respective first EIS and second EIS being performed at least twice for at least two different ones of the given points and resulting in respective assay run indications of measurement states, wherein the selection of the countermeasures is performed based on a combination of the respective assay run indications of the measurement states.

Thus, an assay run indication is an indication on a measurement state that is based on the assessment of at least two different EIS. This may help to further narrow down the possibilities in identifying the system reagents or components that are in an irregular condition.

For example, the at least two given points are comprising the fifth point, the method further comprising
    carrying out the measurement cycle in a prepare run process using a liquid sample void of any analyte and performing a third EIS at the fifth point of the measurement cycle, the third EIS being performed using the working electrode,
    comparing the result of the first EIS obtained for the fifth point and the third EIS,
    providing a prepare run indication of the measurement state indicating if the comparison results that a deviation between the first EIS and the third EIS obtained at the fifth point is exceeding a predefined threshold, wherein the selection of the countermeasures is performed further based on a combination of the respective assay run indications of the measurement states and the prepare run indication.

The combination of the EIS obtained from the fifth point and a further point may thus permit to distinguish between reasons for a possible ECL measurement failure. For example, in case
    the assay run indication obtained for the first, second or third point is positive,
    the assay run indication obtained for the fifth point is negative, and
    the prepare run indication obtained for the fifth point is negative, the selected countermeasure comprises either displaying via the display unit an instruction to replace the current cleaning solution with a cleaning solution of a different lot unit, the display unit being part of the measurement apparatus, the measurement apparatus being part of the measuring cell, or
the selected countermeasure comprises an automated cleaning of components of the apparatus that are used for performing the cleaning of the measuring cell and the working electrode.

Thus, this embodiment may thus allow identifying irregularities in the cleaning solution as a possible cause for an ECL measurement failure or problem. In the present disclosure this will also be referred as a problem caused by an irregular condition of the cleaning solution.

In a further example, in case
    the assay run indication obtained for the first, second or third point is positive,
    the assay run indication obtained for the fifth point is negative, and
    the prepare run indication obtained for the fifth h point is positive,
the selected countermeasure comprises either displaying via the display unit an instruction to replace the current liquid sample containing the analyte with a new liquid sample containing the analyte, or a request for an automated provision of a further liquid sample containing the analyte.

Thus, this may allow to identify a sample with a 'bad' incubate. The quality of a sample may be bad for example due to contaminations within the sample or the analyte.

In accordance with an embodiment of the invention, the method further comprises providing a co-reactant solution to the measuring cell which in combination with the complex permits for the electrochemiluminescence reaction, wherein a first determination is made if a criterion is fulfilled in that
the assay run indication obtained for the first or third point is negative, or
the assay run indication obtained for the second point is negative while at least a further assay run indication obtained for the first, third or fifth point is also negative, wherein in case it is determined by the first determination that the criterion is fulfilled, the selected countermeasure comprises either displaying via the display unit an instruction to clean the components of the apparatus that are used for providing the co-reactant solution to the measuring cell, the display unit being part of the measurement apparatus, the measurement apparatus being part of the measuring cell, or
the selected countermeasure comprises an automated cleaning of components of the apparatus that are used for providing the co-reactant solution to the measuring cell.

Thus, a contaminated or 'bad' co-reactant solution may be identified in this manner. This is also referred to as a problem caused by an irregular condition of the co-reactant solution.

In accordance with an embodiment, after completion of the countermeasure an immediate subsequent repetition of steps b., c. and d. is performed. Then, a second determination is made if the criterion is fulfilled in that
the assay run indication obtained for the first or third point is still negative, or
the assay run indication obtained for the second point is negative while at least a further assay run indication obtained for the first, third or fifth point is also negative, wherein in case it is determined by the second determination that the criterion is fulfilled the selected countermeasure comprises either displaying via the display unit an instruction to clean the measuring cell using an alkaline solution, the display unit being part of the measurement apparatus, the measurement apparatus being part of the measuring cell, or
the selected countermeasure comprises an automated liquid flow cleaning of the measuring cell using an alkaline solution.

In accordance with an embodiment, in case
the assay run indication obtained for the first, third or fifth point is positive,
the assay run indication obtained for the second point is negative,
the selected countermeasure comprises either displaying via the display unit an instruction to clean the components of the apparatus that are used for the provision of the liquid sample containing the analyte to the measuring cell, the measurement apparatus being part of the measuring cell, or
the selected countermeasure comprises an automated cleaning of components of the apparatus that are used for the provision of the liquid sample containing the analyte to the measuring cell and/or a mechanical calibration of the apparatus.

In accordance with an embodiment, the method further comprises comparing said second EIS at the given point for example used for the first or second determination with a respective second EIS obtained for the same given point in an n to last subsequent run of the electrochemiluminescence measurement cycle, n being a variable in between 1 and 1000, wherein the selected countermeasure is only performed in case a comparison of the result of the second EIS obtained for the present and the n to last subsequent run of the electrochemiluminescence measurement cycle results in a deviation exceeding a predefined first aging threshold.

This may generally allow assigning the obtained assay run indications to different reasons: one reason may be the spontaneous occurrence of an error due to a contamination of the respective components of the apparatus. Another reason may be that a negative assay run indication may be the result of an aging of the measuring cell. The aging results in a continuous deviation of the actually obtained EIS from the respective EIS obtained during the calibration process. The older the measuring cell, the stronger the deviation may be.

However, a deviation of EIS due to aging may still be allowable, while a spontaneous deviation is an indication of a problem that has to be attributed to a different source than aging. For this reason, not the absolute deviation of the second EIS at the given point from the first EIS at said given point (obtained some time ago during a calibration process) may be considered. Contrary, the relative deviation of second EIS among themselves may have a higher relevancy here.

Nevertheless, also considering a possible aging limit, the selected countermeasure may only performed in case a comparison of the result of said second EIS at the given point used for the first or second determination with a respective first EIS obtained for the same given point results in a deviation below a predefined second aging threshold. The second aging threshold may therefore be a threshold relative to the original calibration of the EIS. Thus, in case the measuring cell is getting too old, this may also be detected by the method. Accordingly, a respective alternative countermeasure may be initiated upon detecting of an unacceptable aging of the cell. The countermeasure may be the displaying via the display unit an instruction to renew certain components of the measuring cell that are sensitive to aging. Such components may comprise first and foremost the counter and the working electrodes.

Aging of the measuring cell may be determined using any given point in the above mentioned measuring cycle.

In another aspect, the invention relates to an apparatus for performing an electrochemiluminescence method of detecting an analyte in a liquid sample using a measuring cell, the apparatus comprising the measuring cell, the measuring cell comprising a working electrode for detecting the analyte using an electrochemiluminescence measurement cycle, the apparatus comprising a processor and a memory, the memory comprising computer executable instructions, execution of the instructions by the processor causing the apparatus to:
  a. carrying out the measurement cycle in a calibration process using a liquid sample void of the analyte and performing a first electrochemical impedance spectroscopy, EIS, at a given point of the measurement cycle, the first EIS being performed using the working electrode,
  b. carrying out the measurement cycle in an analysis process using the liquid sample containing the analyte and performing a second EIS at the given point of the measurement cycle, the second EIS being performed using the working electrode, c. comparing the result of the first EIS and the second EIS,
d. providing an indication of a measurement state indicating if the comparison results that a deviation between the first EIS and the second EIS is exceeding a predefined threshold.

In another aspect, the invention relates to a computer program product comprising computer executable instructions to perform the above described method.

Embodiments of the invention may be applicable to various kinds of luminescence techniques, including chemiluminescence and electrochemiluminescence, in particular ECL-BBA.

Embodiments of the invention may thus allow detecting in situ several important issues relevant in chemiluminescence measurement cycles: it may allow detecting irregularities in the condition of system reagents, unwanted electrode binding of incubate components, anomalies in incubate transport and aged measuring cells. Generally, a single frequency measurement at 10 kHz may be sufficient to characterize the system. Such a measurement can be performed on sub-second timescale. EIS does not perturb the system as the applied alternating voltage is very small. Further, the required instrumentation can be simple and cheap—low cost FRA can be integrated into the potentiostat of existing ECL systems.

BRIEF DESCRIPTION OF THE DRAWINGS

In the following embodiments of the invention are described in greater detail by way of example only making reference to the drawings in which:

FIG. 4a shows a two wire electrode configurations used for performing the ECL measurement, FIG. 4b shows a three wire electrode configuration used for performing the ECL measurement, FIG. 4c shows a two wire configuration (2 wire configuration) and a 4 wire configuration (4-wire sensing method) used for performing the ECL measurement, FIG. 5 is a decision table that provides countermeasures based on combinations of measurement states (cleaning solution (CIS); co-reactant solution (CoS); measurement cell (MC))

DETAILED DESCRIPTION

Figure 1:
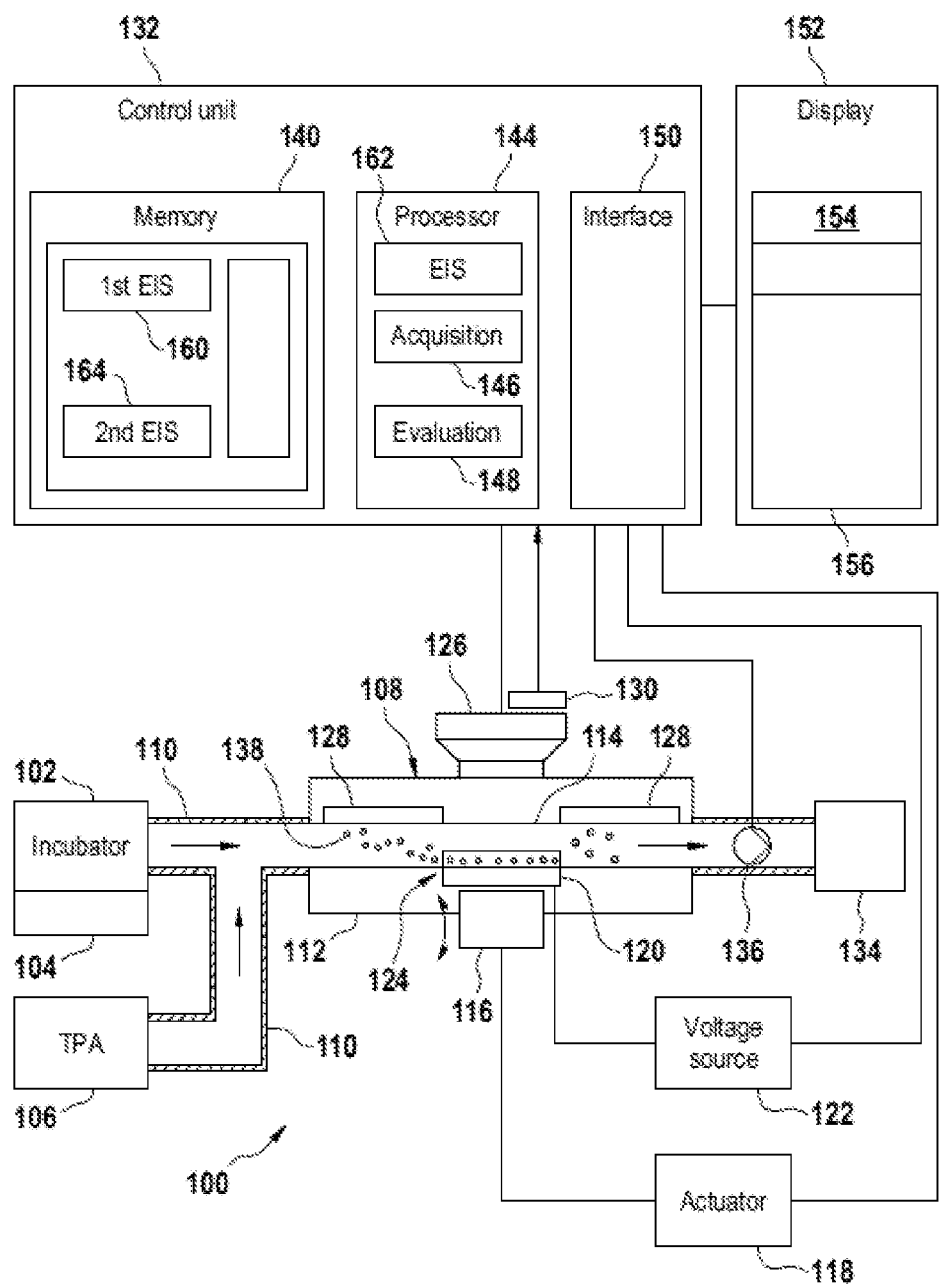
FIG. 1 is a block diagram of an embodiment of an analysis system of the invention.

Throughout the following description of embodiments of the invention like or identical elements will be designated by identical reference numerals.

FIG. 1 shows an analysis system 100 for detecting an analyte in a liquid sample. The analysis system is also designated as the 'measurement apparatus'. The analysis system 100 comprises an incubator 102 for receiving a liquid 104 that is a mixture of an aliquot of the liquid sample and a marker for marking the analyte, such as of a luminescence immunoassay.

The analysis system 100 comprises a reservoir 106 that contains the co-reactant of the electrochemical reaction causing the luminescence. The incubator 102 and the reservoir 106 are coupled to a measuring cell 108 of the analysis system by a pipe system 110 through which a portion of the liquid 104 and the co-reactant can flow into the measuring cell 108.

The measuring cell 108 comprises a cell body 112 that has a conduit 114 for receiving a portion of the liquid 104 and of the co-reactant through the pipe system 110. The measuring cell 108 has a magnetic component 116, such as a permanent magnet, for providing a magnetic field in the measuring cell. The magnetic component 116 may be coupled to an actuator 118 for rotating the magnetic component 116 to and from the conduit 114 in order to switch on or off the magnetic field within the conduit.

The magnetic component 116 is positioned below a working electrode 120 that is coupled to a voltage source 122. An excitation area 124 is formed in the conduit 114 within the magnetic field caused by the magnetic component 116 on the working electrode 120.

Luminescence that is caused in the excitation area 124 by the application of excitation energy, i.e. the application of a voltaic trigger pulse on the working electrode 120, is measured by means of an optical sensor, such as a photomultiplier 126. The optical sensor is sensitive within a certain frequency range such that it provides a measurement signal to which an interfering signal may contribute, such as a luminescence signal caused by autoluminescent molecules that may be present in the measuring cell, provided that the luminescence is within the sensor's frequency range.

The photomultiplier 126 is positioned opposite to the excitation area 124 over a window formed by counter electrodes 128 of the working electrode 120 through which the luminescence photons and any interfering photons caused by the excitation energy impinge on the photomultiplier 126. A resultant time resolved measurement signal 130 is provided from the photomultiplier 126 to a control unit 132 of the analysis system 100.

After a measurement has been performed the liquid contained within the conduit 114 is removed into a liquid waste container 134 and the measuring cell 108 is regenerated for a subsequent acquisition of a measurement signal.

The control unit 132 is coupled to the voltage source 122 in order to control the voltage source 122 to apply the trigger signal to the working electrode 120. The control unit 132 is also coupled to the actuator 118 for controlling the actuator 118 to switch on and off the magnetic field by moving the permanent magnet correspondingly.

Further, the control unit 132 may be coupled to a 'sipper unit', i.e. a pump 136, for extracting a portion of the liquid 104 from the incubator 102 and a portion of the co-reactant from the reservoir 106 as well as for removing the liquid from the measuring cell 108 and regeneration of the measuring cell. In addition the control unit 132 may be coupled to additional robotic components such as a pipetting station.

The measuring cell 108 may be adapted for performing ECL-BBA using various luminescence immunoassays.

Even though ECL-BBA is discussed in the following, this is only an example and this example may be extended by the skilled person to other ECL techniques.

For example, the liquid 104 may contain a mixture of an aliquot of the liquid sample, streptavidin coated magnetic particles, biotinylated antibodies and ruthenylated antibodies to form a so-called 'sandwich' whereas the co-reactant contained in the reservoir 106 is tripropylamine (TPA). Hence, magnetic particles 138 with a bound label flow into the conduit 114. The magnetic particles 138 are immobilized on the working electrode 120 when the magnetic field is switched on. Next, the trigger pulse is applied on the working electrode 120 to cause the electrochemiluminescence in accordance with the ECL-BBA technique.

The control unit 132 has an electronic memory 140 for storing reference data that describes the luminescence decay of a valid measurement signal without a superimposed interfering signal. That reference data is specific for the luminescence immunoassay that is utilized for the detection of the analyte.

In the embodiment considered here the reference data is stored in a lookup table or database table. The reference data comprises a reference dataset for each luminescence immunoassay supported by the analysis system 100. For example, for each supported immunoassay two coefficients a and b as well as a time t is stored in the memory. The coefficients a and b describe a linear law relating the maximum amplitude of the luminescence signal to a luminescence level reached after the decay time t. Storing the decay time t as part of the reference data may be superfluous if the considered decay time t is always the same.

The control unit 132 has at least one electronic processor 144 for execution of program modules 146, 148 and 162. Program module 146 is executed by the processor 144 for acquisition of the measurement signal 132 whereas the program module 148 is executed by the processor 144 for evaluation of the acquired measurement signal 132. Program module 162 is executed by the processor 144 for acquisition of EIS data.

The control unit 132 has an interface 150 for coupling a display unit (or display) 152 or another human-machine-interface to the control unit 132. The interface 150 may be implemented as a graphical user interface for displaying a window 154 for a user's selection of one of the luminescence immunoassays supported by the analysis system 100 as well as a window 156 for displaying a result of the analysis.

The result of the analysis performed by the analysis system 100 may be output as tabular data with one column indicating the analyte to be detected and another column indicating the concentration of the analyte that has been detected. A further column may serve to indicate whether the detected concentration may be erroneous such as by displaying a flag or other warning signal or symbol, such as a red question- or exclamation mark.

Figure 2:
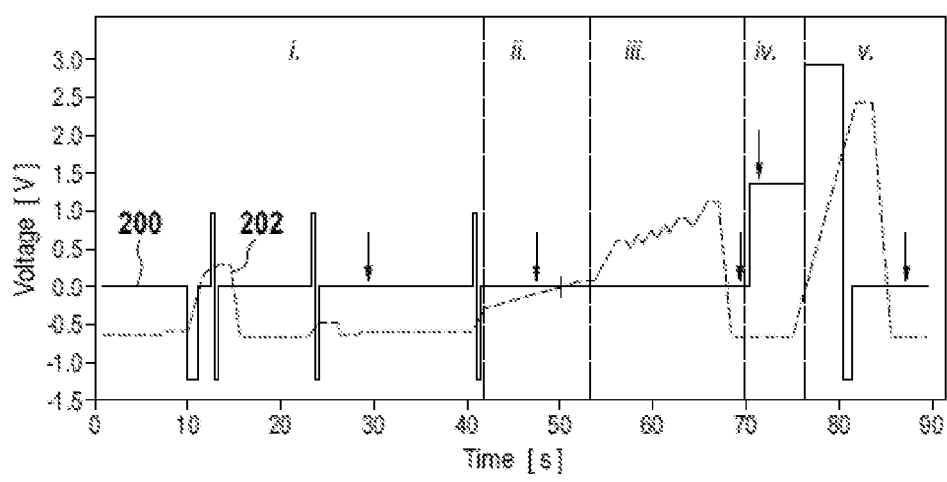
FIG. 2 is a timing diagram being illustrative of the ECL-BBA technique.
Figure 3:
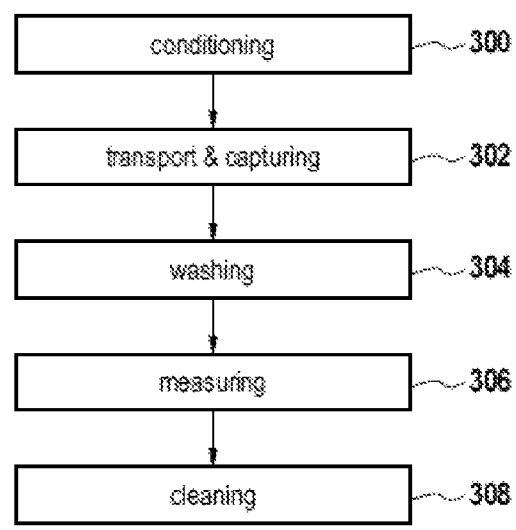
FIG. 3 is a flow chart describing the ECL-BBA technique.

In the following, the ECL-BBA technique will be described in combination with FIGS. 1, 2 and 3. FIG. 2 is a timing diagram showing the different phases of ECL-BBA and FIG. 3 is a respective flow chart.

The method starts in block 300 (phase i) which is a conditioning phase in which a DC potential is applied with certain voltage pulses. The solid line 200 in FIG. 2 is the potential profile applied at the Working electrode (WE, 120) with respect to the Reference electrode (RE). The conditioning has the purpose of preparing the working electrode for the subsequent measurements—conditioning is used to insure that the electrode has a known surface state at the start of the subsequent measurements.

In operation a user selects one of the luminescence immunoassays supported by the analysis system 100 by entering a respective selection into the window 154. The analysis of the liquid sample is started by execution of the program module 146 such that the pump 136 is controlled to transport a portion of the liquid 104 and of the co-reactant into the conduit 114. Line 202 in FIG. 2 designates the movement of any liquid transported via the pump 136 into and out of the measuring cell 108. In fact, the dashed line 202 is the movement of the dilutor piston of the pump 136 that moves the liquid through the cell.

Next, the actuator 118 is controlled to flip the permanent magnet into a position such that its magnetic field is applied to the conduit 114 for immobilization, i.e. capturing of the magnetic particles with their bound labels on the working electrode 120. The process of transport of the liquid and capturing of the magnetic particles is designated with block 302 and corresponds to phase ii in FIG. 2.

Next, in block 306 (phase iv) the voltage source 122 is controlled to apply the trigger pulse onto the working electrode for excitation of the luminescence such that the measurement signal 130 results.

The measurement signal 130 is acquired by sampling the output of the photomultiplier 126 over a given period of time, such as 2 seconds after application of the trigger pulse by the voltage source 122, for time-resolved measuring of the luminescence.

The data samples that constitute the measurement signal 130 are stored within the memory 140 of the control unit 132 and the program module 148 is started for evaluation of the acquired measurement signal 130. By execution of the program module 148 the amplitude of the measurement signal 130 is determined. Next, program module 148 per-forms a read access to the reference data 142 by reading the coefficients a and b of the user-selected immunoassay as well as the time t.

By means of the linear law described by a and b the expected signal level reached by the measurement signal 130 after time t is calculated and compared to the actual signal level of the measurement signal 130 after that time t. In case of a mismatch, i.e. if the actual signal level of the measurement signal 130 is a predefined margin below or above the expected signal level, a mismatch and thus the presence of a superimposed interfering signal is detected.

Next, the concentration of the analyte, if any, in the liquid is determined by the program module 148 by means of the measurement signal 130 and the determined concentration is flagged by an error signal if the mismatch has been detected.

Next, in block 308 (phase v) the pump 136 is controlled by the control unit 132 for removing the liquid from the conduit 114 and regeneration of the measuring cell 108.

An optional washing step (block 304 and phase iii) in between the capturing (block 302) and measuring (block 306) may be performed in order to ensure that the marking substance bound to magnetic microparticles which are not yet attached to the magnet are removed prior to performing the ECL measurement in block 306.

In order to provide a possibility to in situ, i.e. without interruption or disturbing of the above described (ECL) analyte concentration detection, determine the reliability of the analyte detection, the measurement apparatus 100 is further adapted for performing electrochemical impedance spectroscopy, EIS. The EIS is performed using the voltage source 122 and the counter electrode 128. The electronic processor 144 is thus further adapted for execution of the program module 162 for acquisition of EIS signals. For that purpose the voltage source 122 is controlled to overlay an AC current signal onto the DC signal that is used to perform the ECL measurement as described above.

EIS spectra can be acquired at given points of the measurement cycle discussed above and depicted in FIG. 2. For that purpose, the measurement cycle is first carried out in a calibration process using a liquid sample void of the analyte. In this calibration process, a first EIS is performed at a given point of the measurement cycle using the working electrode. Examples of said given point are depicted in FIG. 2 by arrows. The first EIS is then stored in the memory 140 as first EIS data 160.

During the measurement cycle in an analysis process using the liquid sample containing the analyte, a further second EIS is performed at said given point. This results in second EIS data 164 that is stored in the memory. Then, the result of the first EIS and the second EIS are compared and an indication of a measurement state is provided indicating if the comparison results that a deviation between the first EIS and the second EIS is exceeding a predefined threshold.

For example, the measurement state is provided as a graphical output on the display 152. The control unit 132 may further be adapted to automatically accordingly select a countermeasure to correct for a failure of the analysis system 100. After initiation of the countermeasure, the measurement cycle is repeated in the analysis process and another second EIS is performed at the given point to check, if the countermeasure was successful and if the ECL measurement result is reliable or not.

FIG. 4 shows two different electrode configurations used for performing the ECL measurement. The working electrode (WE 120) is the designation for the electrode at which the electrochemical and ECL reactions of interest take place. The Counter or Auxiliary electrode (CE 128) is the electrode in the cell that completes the current path. Both electrodes are commonly made by an inert conductive material such as gold, platinum, glassy-carbon, iridium, boron doped diamond or any other materials which are effective for this purpose.

Any electrochemical cell must have at least a WE-CE pair for operation. This minimal 2 electrode configuration the terminals of the WE and CE are connected to the potential control unit. It is known to a person skilled in the art that in a 2 electrode configuration (2 wire configuration shown in FIG. 4 c) the cell voltage can be quite different from the stimulation voltage $U_{stim}$ and it is at least a function of the cell current and the cable resistance, which is not requested. A calculation for a two electrode configuration is shown in the following Table:

| $U_{stim}$ | $U_{cell}$ | 2 electrode configuration |
|---|---|---|
| 20 mV | 15 mV | $R_{cable}$ = 50 Ω, |
| 10 mV | 5 mV | i = 50 μA, |
| 5 mV | 0 mV (!) | 2 · iR = 5 mV |

For high precision measurements the 4-wire sensing method is used. Here, separate pairs of current-carrying and voltage-sensing electrodes are used as shown in the FIG. 4a: S1 and S2 are used for the control and measurement of the WE and CE potential respectively. P1 and P2 are used for the control and measurement of current flowing through the respective electrodes. Separation of current and voltage electrodes eliminates the lead and contact resistance from the measurement, thus, allowing higher accuracy.

More commonly an additional third electrode is introduced that serves as a reference electrode (RE). This three electrode configuration is shown in FIG. 4b: the RE provides a reference potential to which the applied voltage $V_0$ of the working electrode is referred. In the three electrode configuration a very low or ideally, no current is flowing through the RE. The RE keeps a stable potential. Typical REs are the silver/silver chloride, saturated calomel, mercury/mercury (mercurous) oxide, mercury/mercury sulfate or copper/copper sulfate electrode. Besides, a pseudo-reference electrode made of platinum, gold, stainless steel or other material can be used. These may however provide a less stable reference potential.

As disclosed above, for high precision measurements the 4-wire sensing method is used for the EIS measurement. The 4-wire sensing method compensates the iR drop at the working electrode and at the counter electrode by 2 additional electrodes (4 wire configuration with sense wire 1 and sense wire 2 in FIG. 4 c) for the EIS measurement (iR compensation). The 4-wire sensing method eliminates potential iR drops (=i $R_{cable}$) within the measuring cables. Very low AC responses applying very low sine amplitudes around 10 mVpp as cell voltage $U_{cell}$ are expected in 4-wire sensing method. A resistance $R_{cable}$ within a measuring cable can decrease the cell voltage significantly. In 4-wire sensing method the applied sine wave potential is equal to the cell potential, because any potential drops are eliminated by the sense wires.

Figure 6:
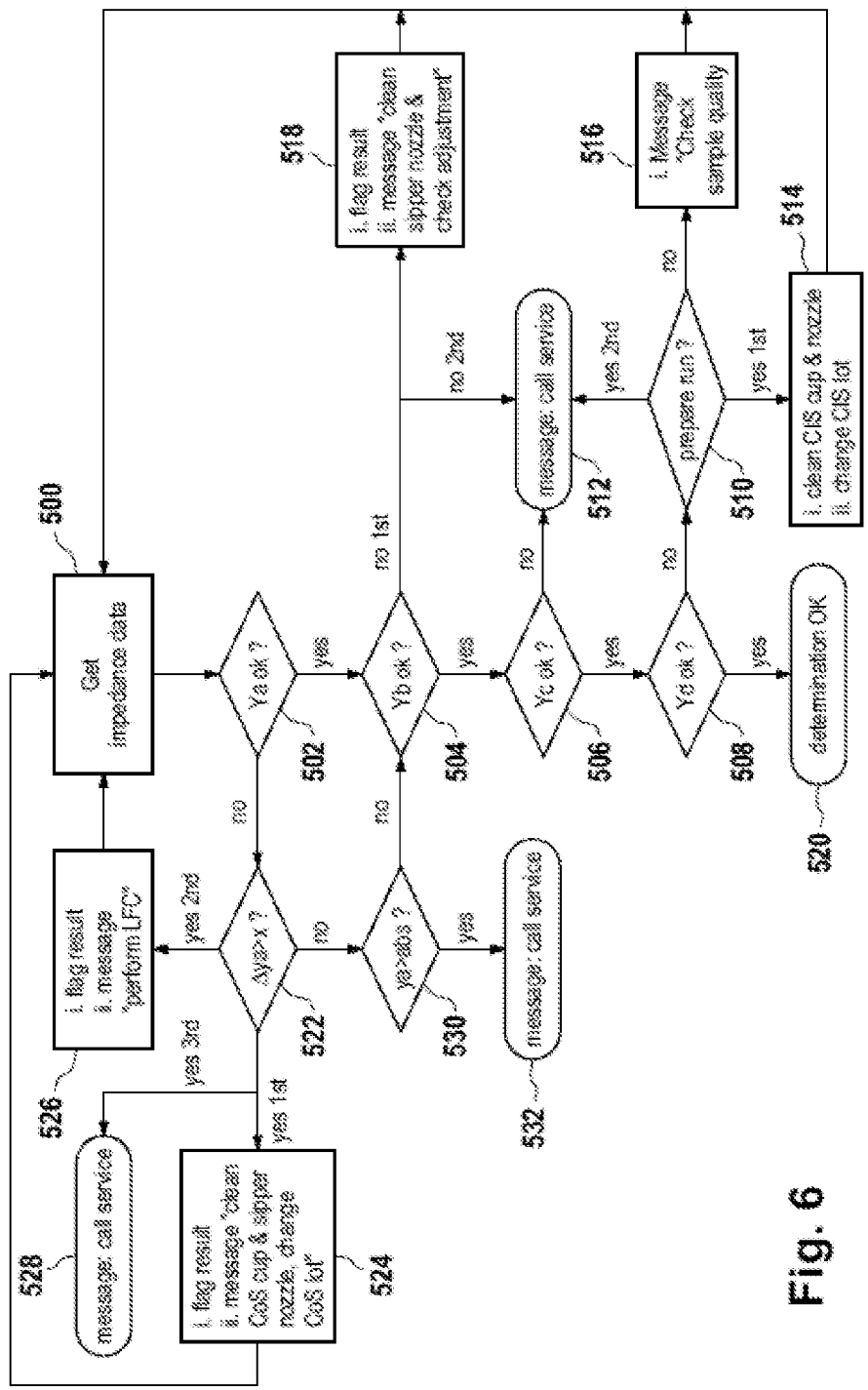
FIG. 6 is a flow chart illustrating a method for performing an ECL method with EIS control (PC=coreactant solution (CoS); CC=cleaning solution (CIS))

FIG. 5 shows a decision table that provides countermeasures based on combinations of measurement states. The flowchart in FIG. 6 illustrates a method that leads to the decisions of FIG. 5. The flowchart of FIG. 6 and the decision table of FIG. 5 are based on the assumption, that for at least two of the above mentioned phases i.-v. an EIS measurement was performed.

For example, for any given point in any of the phases which is indicated by an arrow in FIG. 2, a first EIS was performed in a calibration process when carrying out the measurement cycle. The calibration process assumes in general that the result of the respective first EIS is representative of a system that is behaving as desired. Thereafter, in a subsequent 'real' measurement cycle in an analysis process using the liquid sample containing the analyte, a second EIS is performed at the same given point. The first (calibration) EIS and the second (real sample) EIS are then compared and a measurement state is determined which indicates if the comparison results that a deviation between the first EIS and the second EIS is exceeding a predefined threshold.

Preferably, the measurement states resulting from more than one given point and thus more than two second EIS are then used to determine the reliability of the ECL measurement performed during the measurement cycle of the analysis process.

In order to further fine-tune the method, for example for the given point in phase v. (cleaning of the measuring cell), it is possible to distinguish between a prepare run indication and an assay run indication. For the sake of simple terminology, the assay run indication is identical with the measurement state obtained as described above in an EIS measurement using a real liquid sample. One may define the assay run indication as positive in case the comparison results that a deviation between the compared EIS is within the predefined threshold and as negative in case the comparison results that a deviation between compared EIS is outside the predefined threshold.

Contrary, a prepare run indication is identical with the measurement state obtained as described above in an EIS measurement, however with a liquid sample that is void of any analyte. Thus, in order to obtain the prepare run indication for a given point a third EIS is performed while carrying out the measurement cycle using a liquid sample void of any analyte. Then, this third EIS is compared with the first EIS obtained for the same given point and a measurement state is determined which indicates if the comparison results that a deviation between the first EIS and the third EIS is exceeding a predefined threshold. Again, one may define the prepare run indication as positive in case the comparison results that a deviation between the compared first and third EIS is within the predefined threshold and as negative in case the comparison results that a deviation between compared first and third EIS is outside the predefined threshold.

The variable 'Y' of the flowchart of FIG. 6 is thereby the measurement state. The index a, b, and d are representative of given points indicated by the arrows in FIG. 2 for phase i, ii, v, respectively. Index c is representative of either the given point indicated by the arrow in phase iii. of FIG. 2, or by the arrow in phase iv.

The method starts in block 500 with the acquisition of EIS. It has to be noted, that in FIGS. 5 and 6 the acquisition of second EIS in four phases and the acquisition of a third EIS in phase v. is used. However, it is also possible to reduce the number of used second and third EIS which however may have the disadvantage that problematic or error prone ECL measurements may not be accurately assignable to a certain reason.

After acquisition of the EIS in block 500, it is checked in block 502 if the assay run indication Ya obtained for the first point (arrow in phase i.) is positive. This would indicate that the comparison of the first calibration EIS obtained for said point and the second EIS obtained for said point do not deviate from each other by a value exceeding a predefined threshold.

In case the assay run indication for point 1 is negative, this may be attributed to different reasons. One reason may be an aging of the measuring cell or a contamination of the measuring cell or the involved system reagents or components such as co-reactant solution, cleaning solution and the measuring cell. Aging of the measuring cell continuously degrades the performance of the ECL assay while contamination typically results in a spontaneous change of the ECL assay behavior.

In order to distinguish between aging and contamination of the measuring cell, the method continues with block 522 and the determination, how for the same given point the present second EIS deviates from second EIS obtained from a previous measurement. Thus, the second EIS at the given point is compared with a respective second EIS obtained for the same given point in an n to last subsequent run of the electrochemiluminescence measurement cycle, n being a variable in between 1 and 1000. In case the deviation $\Delta ya$ of the present EIS from the previous EIS is exceeding a predefined aging threshold 'x', this may be attributed to a contamination of the system. This may be understood as a 'sudden jump' of the EIS curve obtained for the present measurement run compared to a previous measurement run.

Contrary, in case the deviation $\Delta ya$ is below the aging threshold, this may be attributed to a continuous aging of the measuring cell. In the latter case, it may be determined in block 530 if the absolute value ya of the difference between the first and the second EIS for said point is exceeding an absolute aging value abs. If this is the case, in block 530 information may be provided by the system for example using the display 152 that the measuring cell has to be exchanged due to aging reasons. More simplified, a message 'call service' may be output.

However, in case in block 530 it is determined that the absolute value ya of the difference between the first and the second EIS for said point is not exceeding an absolute aging value abs, the method continues with block 504 which will be discussed below.

In case in block 522 it is determined that the deviation $\Delta ya$ of the present EIS from the previous EIS is exceeding a predefined aging threshold 'x', the method continuous with either block 524, 526 or 528. Block 524 is chosen in case said deviation occurred for the first time, block 526 is chosen in case said deviation occurred for the second time and block 528 is chosen in case said deviation occurred for the third time. For this reason, the presence of a flag is checked: in case no flag is associated with the second EIS for the given point (or the flag is 1), block 524 will be chosen. In case the flag is set (or the flag is 2), block 526 will be chosen etc.

The selection of blocks 524, 526 and 528 correspond to the preferably automated initiation of countermeasures. For example, in block 524 the flag is set (or increased from 1 to 2) and a message may be output via the display that the cup containing the co-reactant solution and the sipper nozzle used to obtain the co-reactant solution from its reservoir has to be cleaned. Further, the message may recommend to change the present co-reactant solution lot. In a further example, said cleaning and said changing may be automatically initiated and performed by the system. Block 524 corresponds to the third line in the decision table of FIG. 5. After completion of block 524, the method restarts with block 500.

In block 526 the flag is increased from 1 to 2 or from 2 to 3 and a message may be output via the display that a liquid flow cleaning (LFC) of the system has to be performed. Liquid flow cleaning occurs when this function is initiated from the service screen of the instrument. During LFC a sodium hypochlorite solution is aspirated for cleaning of the measuring cells and the flow path. In a further example, said LFC may be automatically initiated and performed by the system. Further, a preferably automated exchange of the measuring cell (MC) may be initiated. Block 524 corresponds to the fourth line in the decision table of FIG. 5. After completion of block 524, the method restarts with block 500.

It has to be noted, that the flag may be realized by any known method which allows distinguishing between the first, second or third time that Δya>x is occurring in a successive manner.

In block 528 information may be provided by the system has an undefined malfunction. More simplified, a message 'call service' may be output. Here, the system will stop and the method will end.

In case in block 502 it was determined that Ya was ok, i.e. that the assay run indication was positive, the method continues with block 504 and the determination, if the assay run indication for Yb is positive or not. Yb is the result of the EIS obtained during or at the end of the provision of the liquid sample to the measuring cell and capturing of magnetic microparticles. Thus, depending if the optional phase iii. is present, Yb may be obtained at the given point indicated by the arrow in phase ii. or phase iv. In case the assay run indication is negative, the method distinguished between the first time and the second time this problem is occurring. For this purpose, the assay run indication again uses a respective flag as it was discussed with respect to Ya.

In case the problem occurs for the first time, in block 518 this may be attributed to a problem with the analyte. For example, the analyte may comprise air bubbles or it may be contaminated. As a countermeasure, a message may be output via the display that the sample quality has to be checked. Further the flag is set (or increased in number). In a further example, the system may automatically obtain a new liquid sample with the same analyte. Block 518 corresponds to the last line in the decision table of FIG. 5. After completion of block 518, the method restarts with block 500.

In case said problem occurs for the second time, block 504 is immediately followed by block 512 which corresponds to block 528.

In case it turned out that in block 504 Yb was ok, the method continues with optional block 506. In block 506 it is determined if the assay run indication for Yc (obtained at the given point indicated with the arrow in phase iii.) is positive or not. Yc is the result of the EIS obtained during the phase for washing of the measuring cell after the capturing and before the electrochemiluminescence measurement. In case Yc is negative, this immediately may result in execution of block 512. The decision with respect to Yc is not reflected in the decision table of FIG. 5 since the cleaning step in phase iii. is optional.

In case Yc is positive or directly after block 504 (Yb ok), the method continues with block 508 and the determination, if the assay run indication for Yd is positive or not. Yd is the result of the EIS obtained during phase v., i.e. during cleaning of the measuring cell with the working electrode with a cleaning solution. In case Yd is ok, the method ends with block 520 and the determination that the ECL measurement is reliable.

However, in case Yd is not ok, block 510 following block 508 determines if the present Yd is the result of an assay run or a prepare run of the measurement cycle. In case it is the result of a measurement run, a message is output according to which the sample quality is to be checked. The system may automatically continue with subsequent block 500 in prepare run, i.e. in a run of the measuring cycle with a liquid sample void of any analyte.

In case the method again arrives in block 510, the method continues either with block 514 in case the prepare run is performed for the first time, or with block 512 in case the prepare run is performed for the second time. First and second time may be checked by means of a flag correspondingly as described above.

Block 514 corresponding to the first line in the decision table of FIG. 5 may output a message according to which the cleaning solution cup, a reservoir on the instrument in which the cleaning solution is dispensed, and the nozzle used to transport the cleaning solution into the measuring cell is to be cleaned and to exchange the currently used cleaning solution lot with a new one. Alternatively or additionally the cleaning and exchanging may be performed automatically. After block 514 the method continues with block 500.

Even though in the discussion with respect to FIG. 6 aging was only considered with respect to phase i, the skilled person will understand that this principle may be accordingly applied to any of the given points in the measuring cycle.

Figure 7:
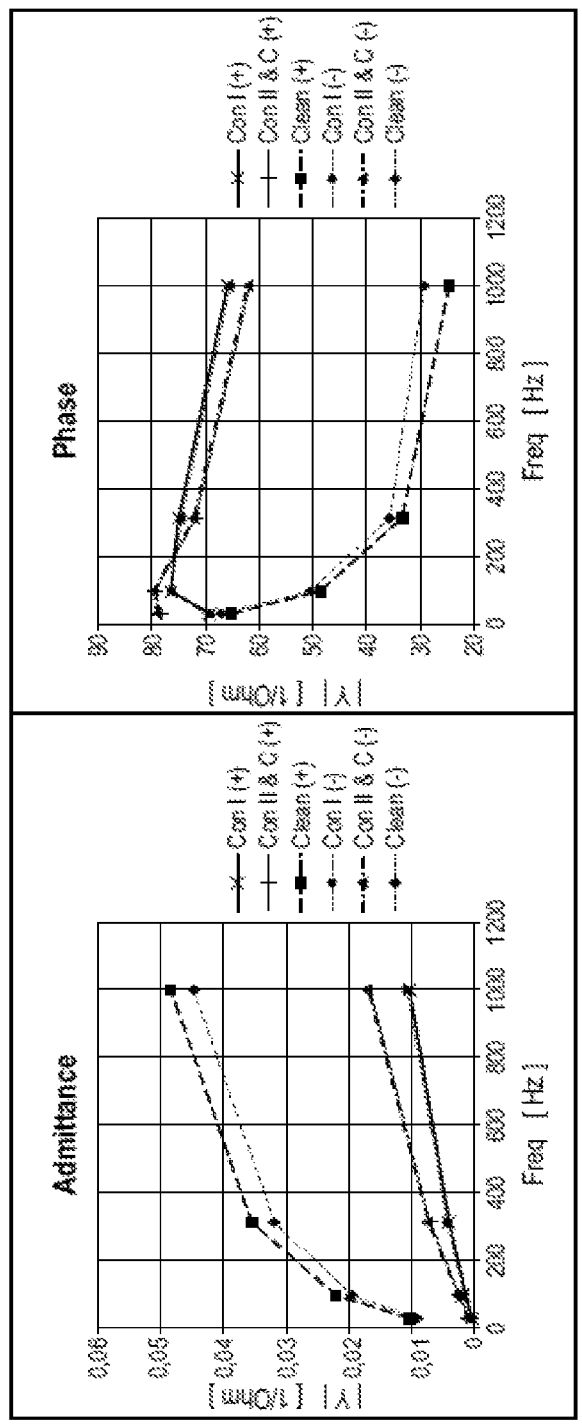
FIG. 7 shows EIS measurement results on admittance and phase for illustrating the effect of a contaminated cleaning solution and a clean cleaning solution.

FIG. 7 shows EIS measurement results on admittance and phase for illustrating the effect of a contaminated cleaning solution and a clean cleaning solution. In order to study the effect of an a cleaning solution in an irregular condition the Streptavidin particles (SAP) assay was measured (n=5) with an contaminated cleaning solution and compared to the results of the SAP assay with flaw-less cleaning solution. The EIS measurements were performed at the points indicated in FIG. 2 for phase i, iv and v. Herein, phase i is designated as 'Con I', phase iv is designated as 'Con II & C' and phase v is designated as 'Clean'. Further, (+) means that the cleaning solution was clean whereas (−) means that the cleaning solution was contaminated. The EIS measurements were performed at 0 Hz, 100 Hz, 300 Hz and 1000 Hz.

It can be clearly seen that for a contaminated cleaning solution can be easily identified in phase v. Here, a strong deviation (>>1SD) between the EIS obtained as calibration data (straight lines) and the EIS obtained for the measurement on the contaminated cleaning solution (dashed lines) is already visible in admittance at 100 Hz. Further, the standard deviation obtained for the measurement points in phase v is far below the deviation between the calibration curve and the measurement curve obtained for the contaminated cleaning solution. This shows that an improper cleaning solution can be easily detected and identified as such.

Figure 8:
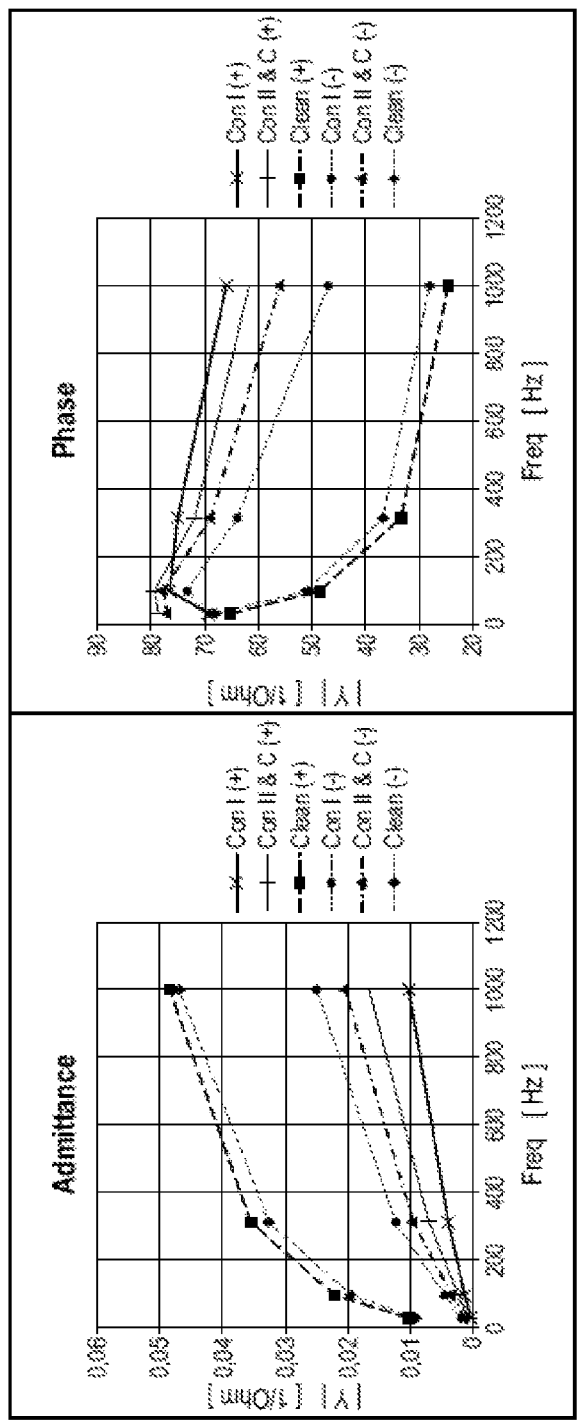
FIG. 8 shows EIS measurement results on admittance and phase for illustrating the effect of a contaminated co-reactant solution and a clean co-reactant solution.

FIG. 8 shows EIS measurement results on admittance and phase for illustrating the effect of a contaminated co-reactant solution and a clean co-reactant solution. In order to study the effect of aco-reactant solution in an irregular condition the Streptavidin particles (SAP) assay was measured (n=5) with an erroneous co-reactant solution and compared to the results of the SAP assay with flaw-less co-reactant solution. The EIS measurements were again performed at the points indicated in FIG. 2 for phase i, iv and v. Herein, phase i is designated as 'Con I', phase iv is designated as 'Con II & C' and phase v is designated as 'Clean'. Further, (+) means that the co-reactant solution was clean whereas (−) means that the co-reactant solution was contaminated. The EIS measurements were performed at 0 Hz, 100 Hz, 300 Hz and 1000 Hz. The dashed lines correspond to the calibration data, the straight lines to the measurement data on the contaminated co-reactant solution.

It can be clearly seen that for a contaminated co-reactant solution can be easily identified in all three phases. A significant change (>>1SD) in the admittance as well as the phase in all steps was observed and allows a clear discrimination between erroneous and flaw-less co-reactant solution. The change is significant at all frequencies considering the admittance. Considering the phase a better discrimination is observed for frequencies higher than ~100 Hz. In general the deviations are strongest in Con I (phase i) but are still visible in Cleaning (phase v).

Figure 9:
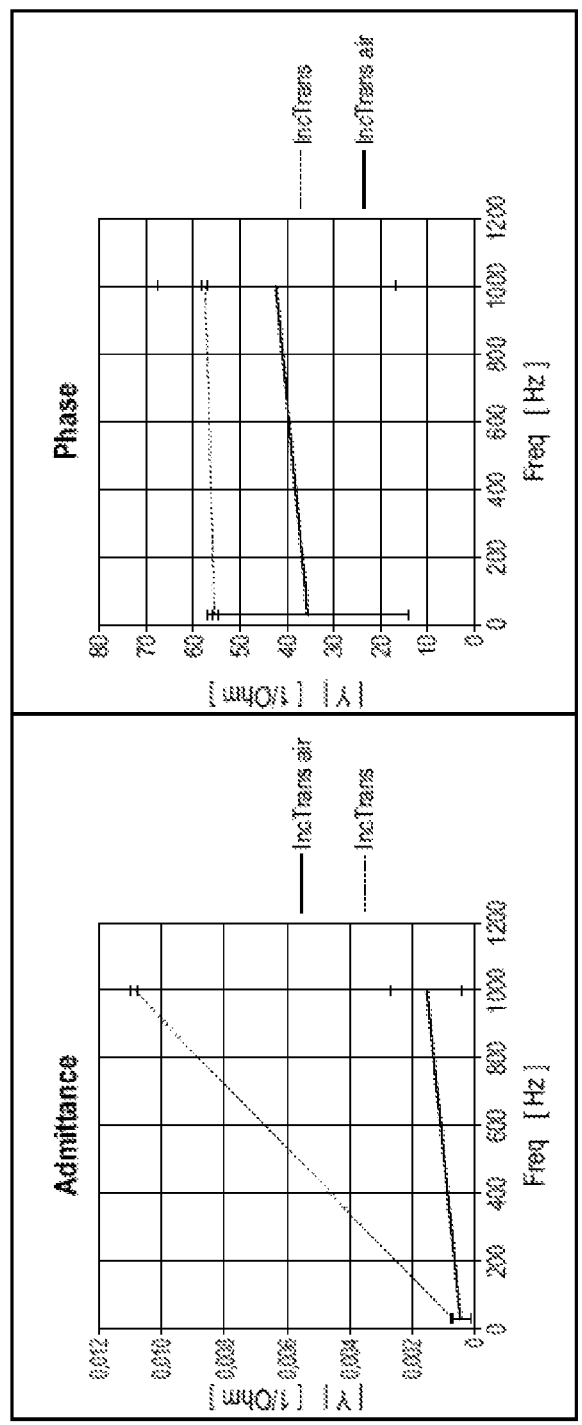
FIG. 9 shows EIS measurement results on admittance for illustrating the effect of a pipetting error of the sample to be analyzed.

FIG. 9 shows EIS measurement results on admittance for illustrating the effect of a pipetting error of the sample to be analyzed. Due to the pipetting error, air is pipetted and transferred into the measuring cell. In phase ii, this results in a significant deviation between the admittance obtained for the EIS calibration (IncTrans) and the EIS obtained on sample with the pipetting error (IncTrans air). The result is a 700% change in admittance and a 60% change in phase due to the presence of air. Thus a malfunctioning pipetting or incubate sipping can be detected.

In the following, a detailed description of EIS measurements are given. All experiments were carried out using a Roche Elecsys® breadboard. This is a highly flexible Elecsys system for development purposes and comparable to an Elecsys® 1010 or 2010. For this study the breadboard was equipped with a SP-300 potentiostat from Bio-Logic Science Instruments SAS, France. The SP-300 is a state-of-the-art modular research grade potentiostat with a built in frequency response analyzer (FRA). Experiments were generally carried out with standard Elecsys measuring cells in the conventional 3 electrode set-up using a working electrode, counter electrode and reference electrode. All potential profiles and according EIS measurements were programmed using the EC-lab software package. Communication between the potentiostat and the Elecsys analyzer was established using the built in "trigger in" channel of the potentiostat. The Elecsys analyzer was then able to control the potentiostat by sending TTL pulses at desired time points.

Measurements were carried out using an artificial immunoassay (SAP)—an assay including RuBpy labeled microparticles for a high specific ECL signal. The protocols for the assays mentioned below were taken as recommend for Roche Elecsys® 2010 with slight adaptations in the volumes. The volume of bead suspension was 35 µl, the volume of free RuBpy conjugate was 15 µl, the volume of bead buffer was 150 µl and the volume of sample was 0 µl.

Figure 10:
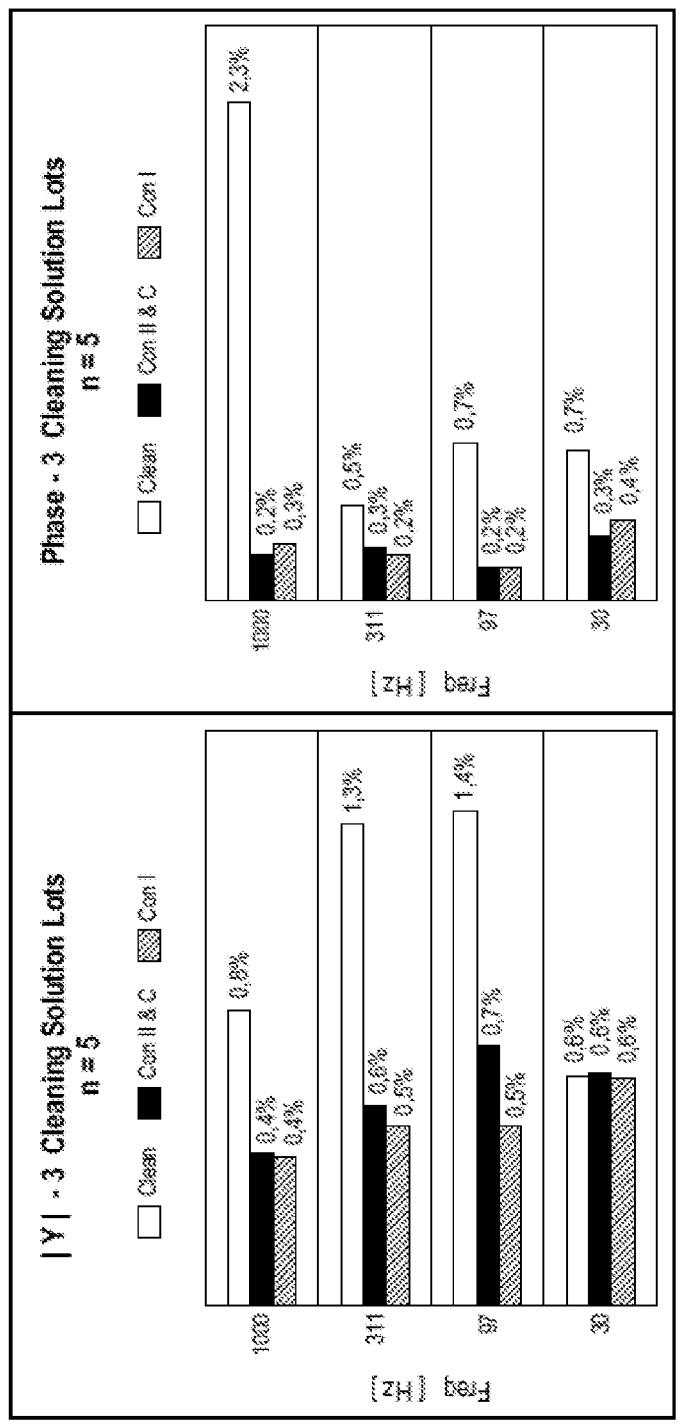
FIGS. 10 and 11 show EIS measuring results that are proving that it is possible to identify irregular conditions of reagents/components such as cleaning solution (FIG. 10), co-reactant solution (coreactant) (FIG. 11) and the measuring cell (MC)
Figure 11:
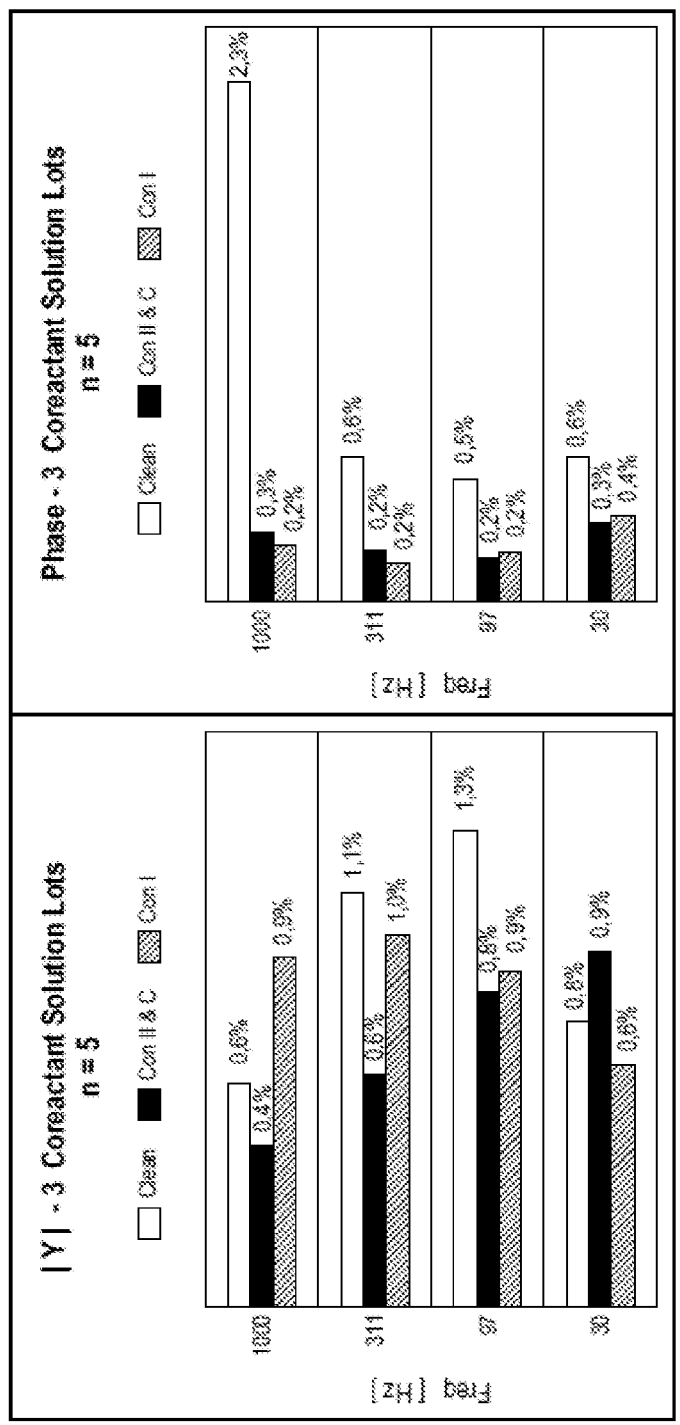

FIGS. 10 and 11 shows EIS measuring results that are proving that it is possible to identify erroneous system reagents/components such as co-reactant solution, cleaning solution and the measuring cell. This requires high reproducibility of the EIS results for measurements of the untainted system. In order to do so the analyzer was equipped with an intact measuring cell and flawless lots of cleaning solution and co-reactant solution.

To also consider the fluctuation that might origin from different lots of co-reactant solution and cleaning solution this experiment was repeated with 3 lots of cleaning solution and co-reactant solution respectively and with n=5 assay determinations of Streptavidin particles (SAP) each. In other words, for a given point the EIS was acquired 5 times per lot and this was repeated three times for different lots. The precision was determined by calculating the CV (ratio of standard deviation and mean value in percent) over all different runs and determinations. The results are reported in FIGS. 10 and 11. FIG. 10 shows a variation of cleaning solution lots and FIG. 11 shows a variation of co-reactant solution lots. As it can be seen from these figures the CV is usually well below 1% proving the high reproducibility of the method.

Again "Clean" stands for the EIS obtained in phase v, "Con I" stands for the EIS obtained for phase i and "Con II & C" stands for phase iv as described above.

In order to determine the effect of the magnetic nanoparticles "beads", the Streptavidin particles (SAP) assay was measured (n=5) and compared to an assay were all reagents in the SAP were replaced by co-reactant solution (CoS). Basically two situations are compared here: in the first case the incubate contains magnetic beads that are captured and deposited on the electrode. In the second case the incubate contains no beads and the electrode remains free after the capturing process. Consequently only a change in admittance is expected after the Cond II & Capt step.

Figure 12:
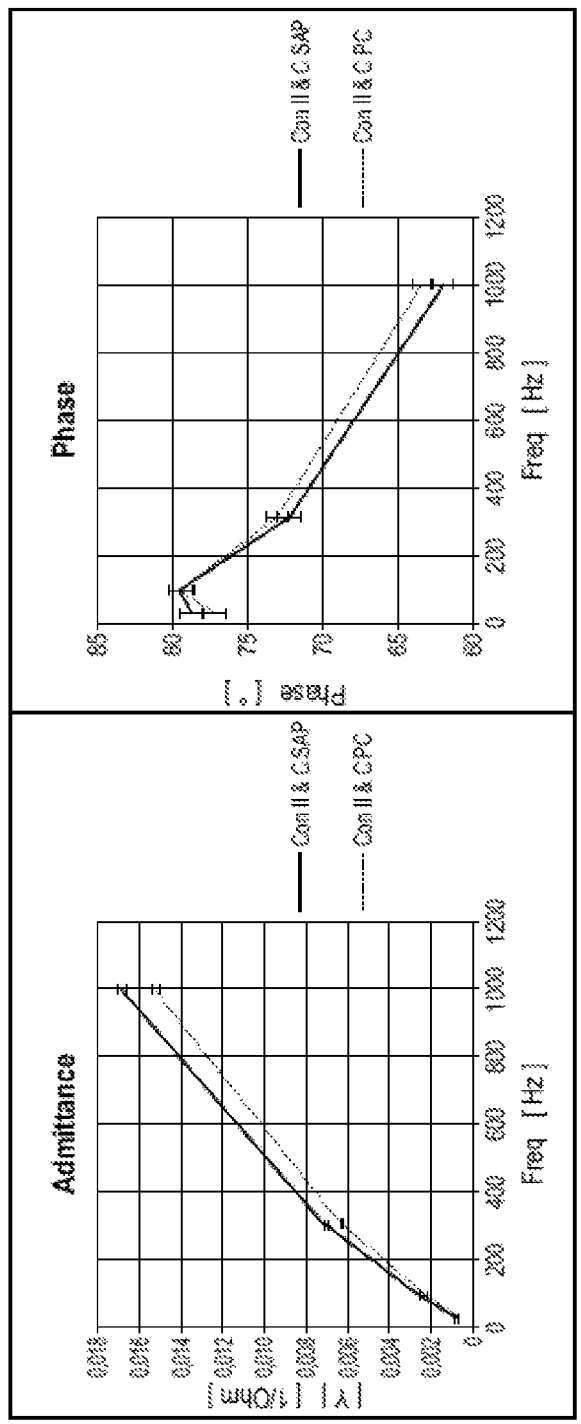
FIG. 12 shows EIS measuring results illustrating the difference between an incubate containing beads and an incubate containing no beads.

As a matter of fact significant changes of standard deviation (>>1SD) are seen in the admittance of the Con II & Capt step (phase iv) at frequencies >100 Hz, as reported in FIG. 12. Similar changes are also observed in the phase (with lower significance due to a higher error). Nevertheless, the measurement gives thus a means to discriminate between an incubate containing beads and an incubate containing no beads.

Figure 13:
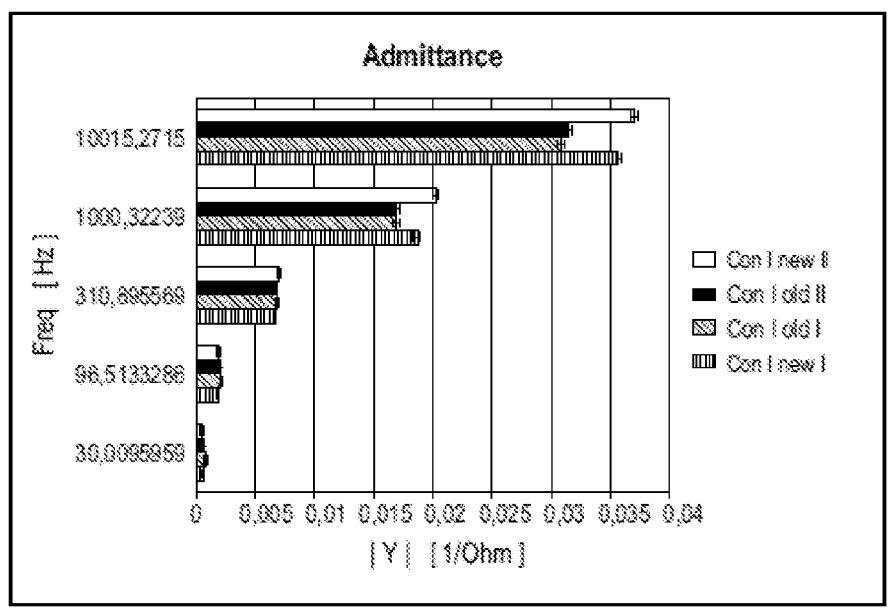
FIG. 13 shows EIS admittance data illustrating the aging of measuring cells in phase i.
Figure 14:
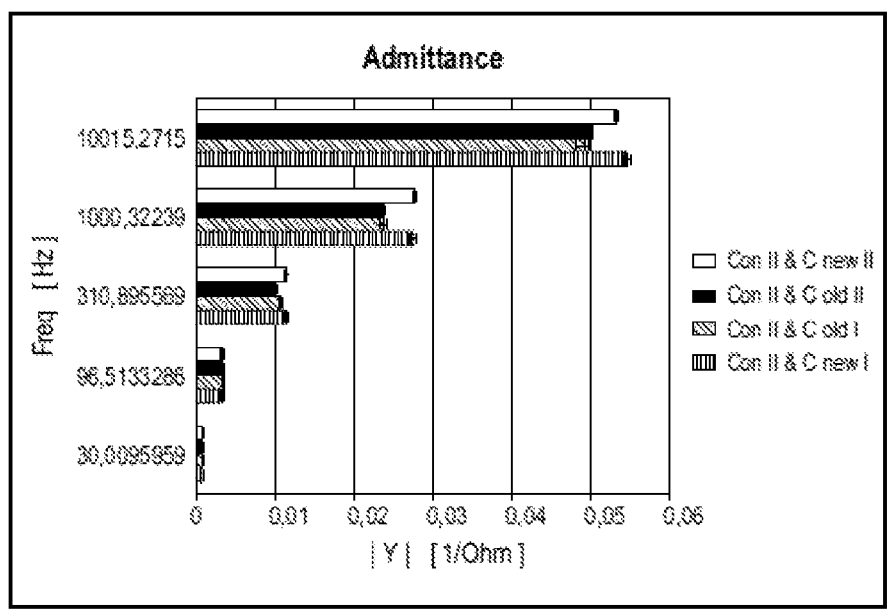
FIG. 14 shows EIS admittance data illustrating the aging of measuring cells in phase iv.
Figure 15:
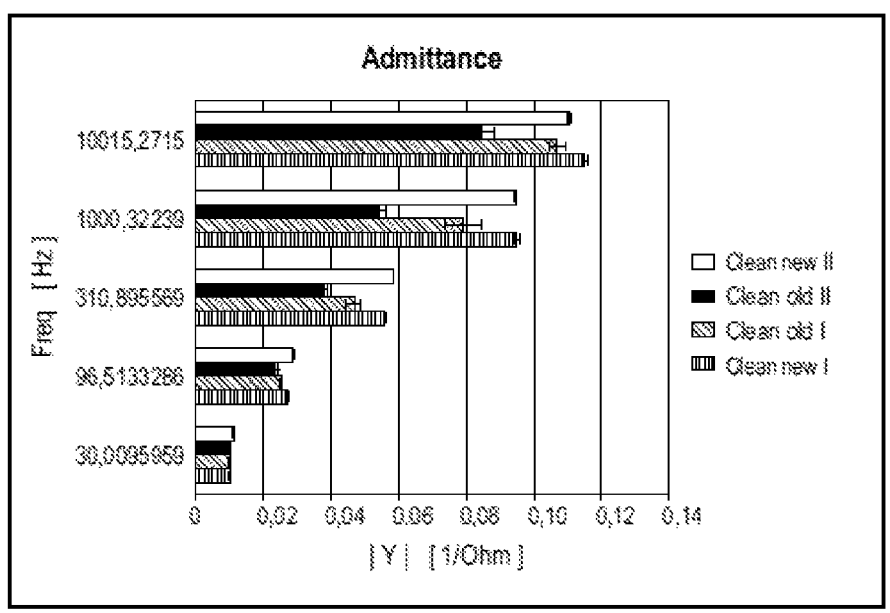
FIG. 15 shows EIS admittance data illustrating the aging of measuring cells in phase v.

Aging of the measuring cell can cause performance loss of the Elecsys assay and is therefore carefully monitored by service technicians using an assay performance check. However, cell age can also be monitored using EIS as shown in the example of FIG. 13. For better visibility the results are plotted here in a bar diagram (in contrast to the curve plots shown in previous figures). Here the EIS spectra of two new measuring cells "new 1" and "new 2" are compared with two significantly aged measuring cells "old 1" and "old 2". Obviously new and old cells can be clearly distinguished in the admittance. The changes are most significant for frequencies 300 Hz. In FIG. 13 the EIS results for phase i are shown. In FIG. 14 the results for phase iv and in FIG. 15 the results for phase v are depicted.

Figure 16:
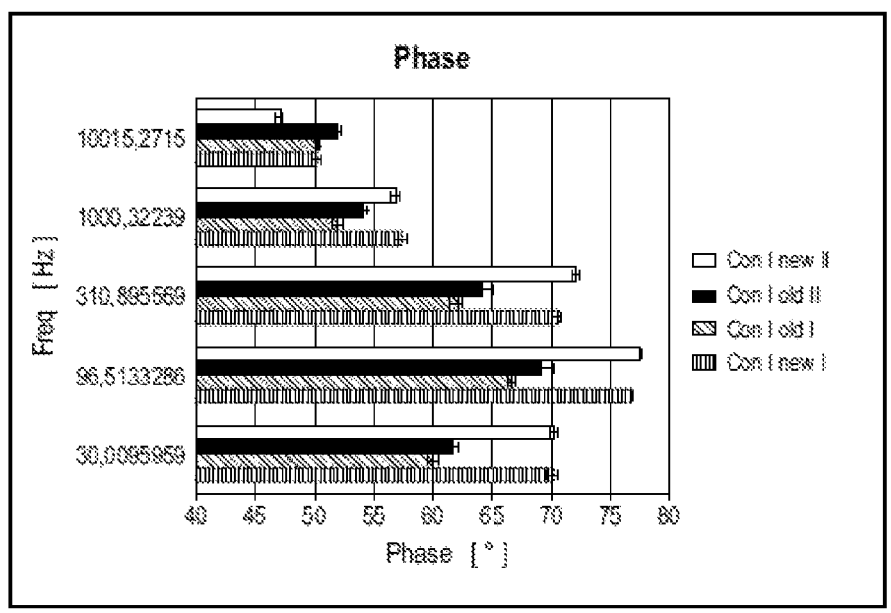
FIG. 16 shows EIS phase data illustrating the aging of measuring cells in phase i.
Figure 17:
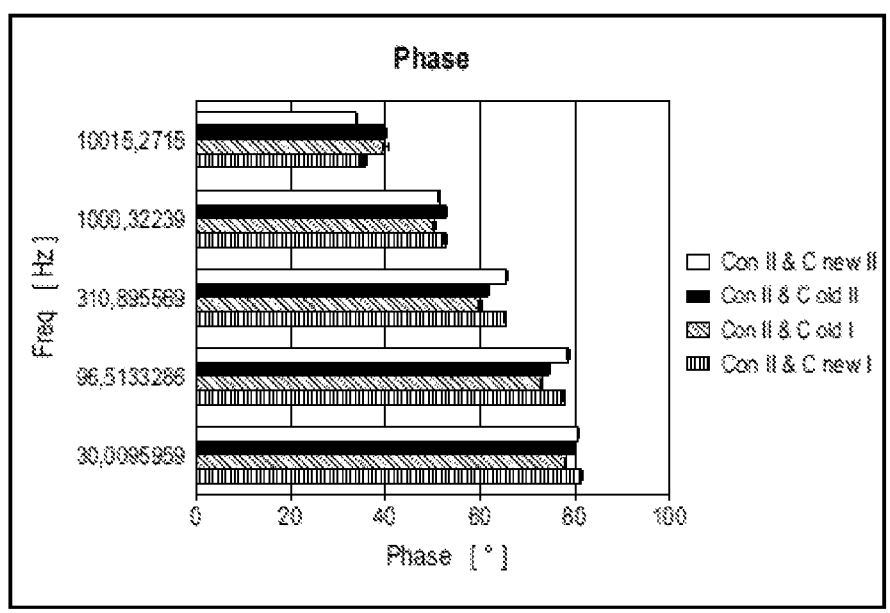
FIG. 17 shows EIS phase data illustrating the aging of measuring cells in phase iv.
Figure 18:
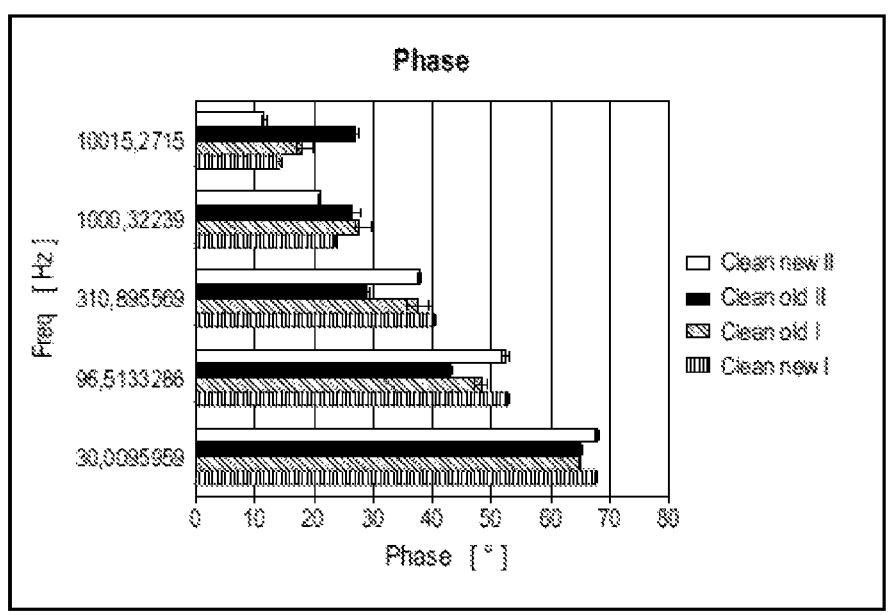
FIG. 18 shows EIS phase data illustrating the aging of measuring cells in phase v.

Also the phase shows a clear discrimination between old and new measuring cells. The changes are most significant for frequencies 1000 Hz for phase i and phase v and 10 kHz for phase iv, compare FIGS. 16, 17 and 18. It has to be noted that the change by cell aging is gradual and can therefore be distinguished from non-aging related processes that cause changes on short timescales.

In the following, the effect of sample components is studied. A prewash procedure "PW" is used to remove any free biotinylated antibody or serum components from the incubate that could interfere with the measurement. During Prewash the streptavidin beads are separated from the buffer using a magnetic microparticle separator. Subsequently the beads are washed with buffer solution (PreClean) and reconstituted to their original volume. The effect of the sample type (that forms part of the incubate) on the EIS spectrum was investigated. To do this the Streptavidin particles (SAP) assay was used and 50 µl of sample were included. The volume of bead suspension was 35 µl, the volume of free RuBpy conjugate was 15 µl, the volume of bead buffer was 150 µl and the volume of sample was 50 µl.

Figure 19:
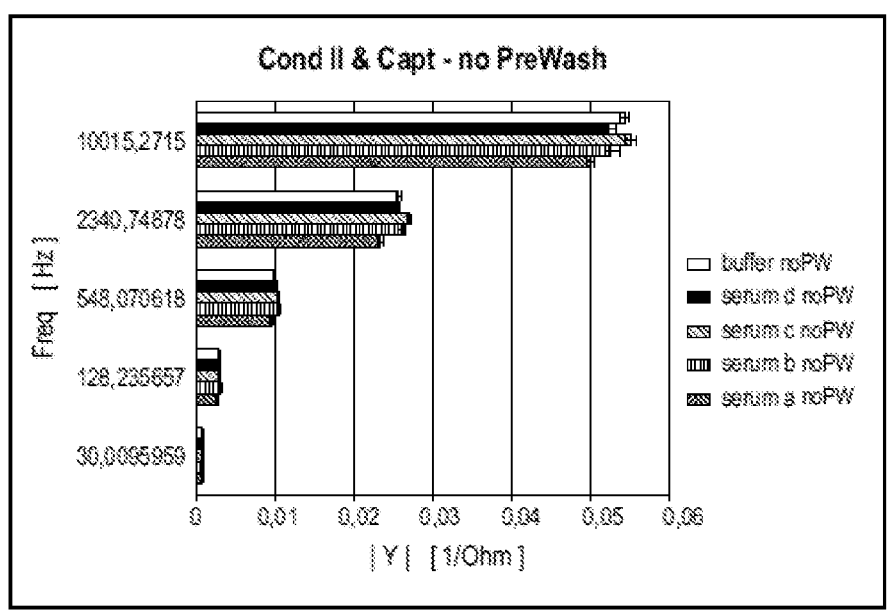
FIG. 19 shows EIS measuring results illustrating in phase iv the difference resulting from sipping comprising no incubates and comprising incubates, with no PreWash being applied.
Figure 20:
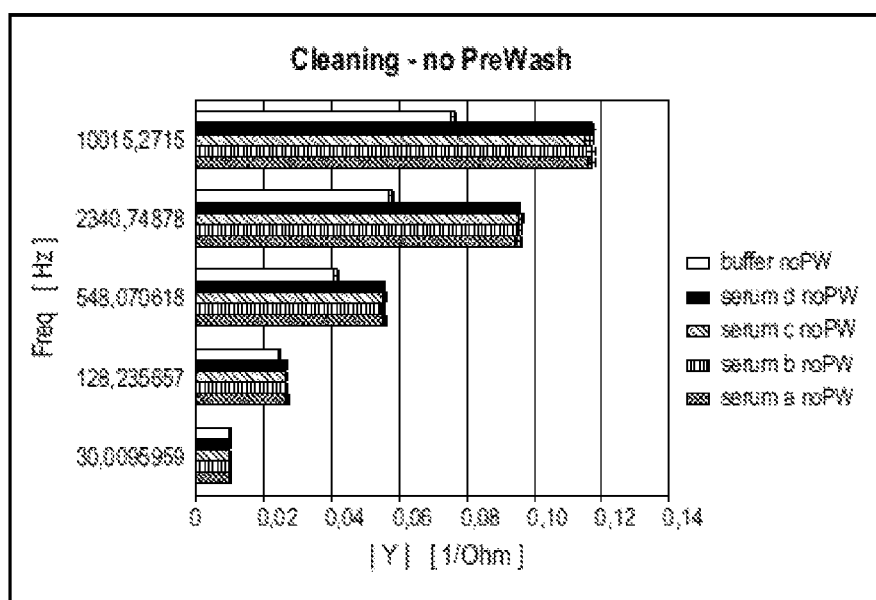
FIG. 20 shows EIS measuring results illustrating in phase v the difference resulting from sipping comprising no incubates and comprising incubates, with no PreWash being applied.

Four different sera were used in order to model different sample types and its effect on the EIS spectra was investigated. In common low throughput Elecsys analyzers such as e411 or e2010 sample components can come into contact with the electrode during the incubate transport. This usually leads to a serum specific adsorption of proteins to the electrode surface. If a serum free incubate (where the sample is replaced by buffer) is compared with incubates containing serum, clear differences are seen in the EIS spectra analyzed in FIGS. 19 and 20. No PreWash was applied here. The serum containing incubate leads to a decrease in admittance in the Cond II & Capt step (phase iv) at frequencies >130 Hz with respect to the serum free incubate. On the other hand a strong admittance increase is seen for the serum containing incubate in the cleaning step (phase v).

Consequently, EIS can be used to monitor the sample pipetting. If no sample is pipetted the incubate it is free of serum components and no adsorption is expected at the electrode. Such an event can be easily spotted by the EIS method as an "anomalous incubate" and a warning can be sent to the operator and/or respective countermeasures can be automatically initiated.

Figure 21:
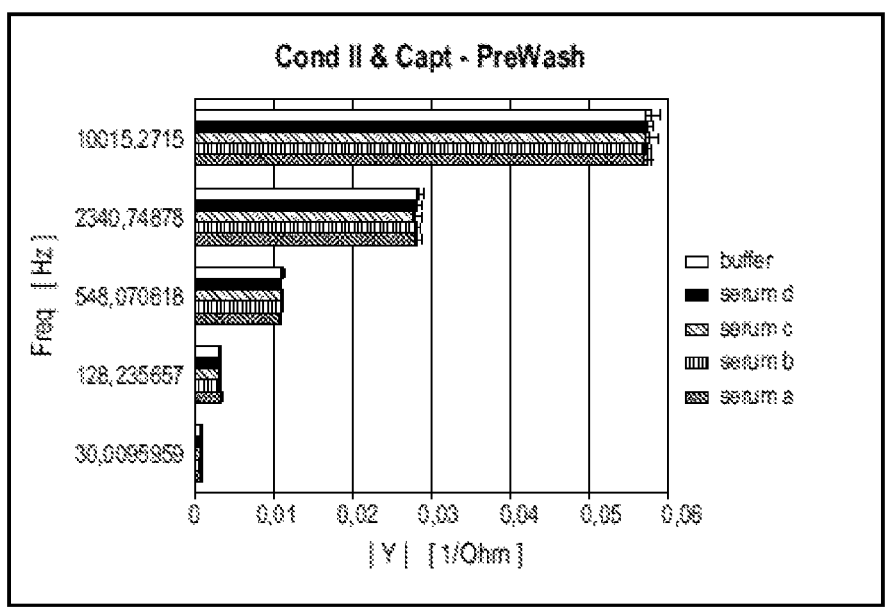
FIG. 21 shows EIS measuring results illustrating in phase iv the difference resulting from sipping comprising no incubates and comprising incubates, with PreWash being applied.
Figure 22:
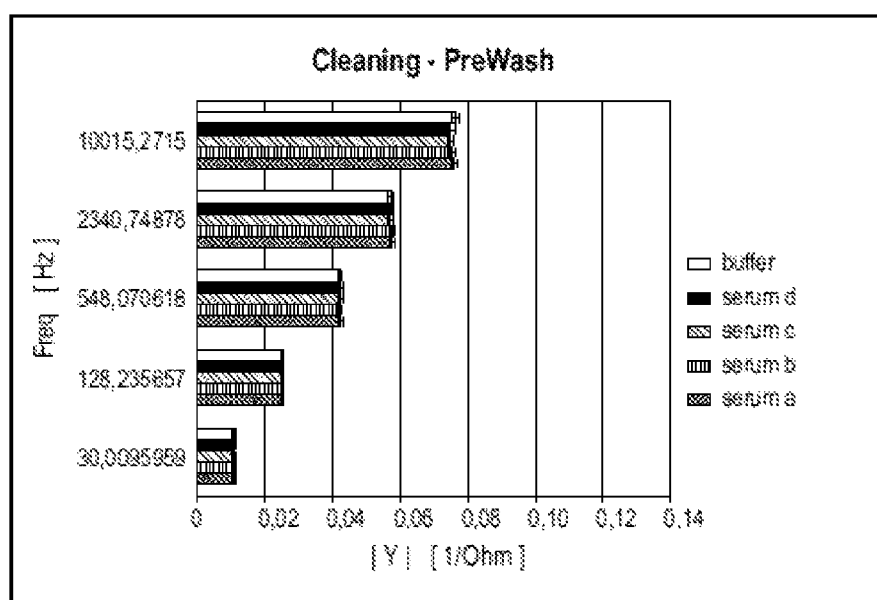
FIG. 22 shows EIS measuring results illustrating in phase v the difference resulting from sipping comprising no incubates and comprising incubates, with PreWash being applied.

High troughput analyzers such e170, e601, e602 and e801 on the other hand make use of a so called PreWash function. During the PreWash the magnetic beads are magnetically captured at the vessel wall. Subsequently, the incubate containing assay reagents and serum is removed and substituted by buffer solution. This "prewashed incubate" is free of serum components. Thus, no differences are expected between the different sample types when EIS spectra are considered after the Cond II & Capt step (phase iv) or the cleaning step (phase v). This can be easily seen from the FIGS. 21 and 22 where the prewashed sera a-d are compared.

Figure 23:
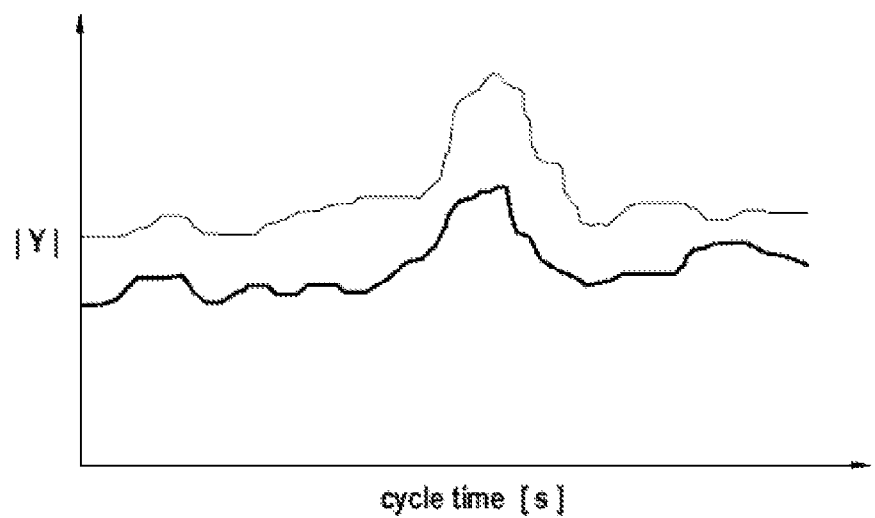
FIG. 23 is illustrative of a continuous EIS measurement.

FIG. 23 is an EIS spectrum that is expected as a result of a continuous measurement over the whole measuring cycle of FIG. 2 at single frequency of 1000 Hz. The measurement result of the admittance of such a continuous EIS is shown in FIG. 26. The lower line corresponds to a measuring cycle in which a flawless co-reactant solution was used, whereas the upper line corresponds to a measuring cycle in which co-reactant solution in an irregular condition was used. An overall admittance shift to higher values can be easily observed in that case.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

LIST OF REFERENCE NUMERALS

Analysis system 100
Incubator 102
Liquid 104
Reservoir 106
Measuring cell 108
A pipe system 110
Cell body 112
Conduit 114
Magnetic component 116
Actuator 118
Working electrode 120
Voltage source 122
Excitation area 124
Photomultiplier 126
Counter electrode 128
Measurement signal 130
Control unit 132
Container 134
Pump 136
Particle 138
Memory 140
Reference data 142
Processor 144
Program module 146
Program module 148
Interface 150
Display 152
Window 154
Window 156
EIS data 160
Program module 162
EIS data 164
Potential profile 200
Movement of the dilutor piston 202

The invention claimed is:

1. A method for indicating the reliability of a method for electrochemiluminescence detection of an analyte in a liquid sample using a measuring cell, the measuring cell comprising a working electrode for generating an electrical field for triggering an electrochemiluminescence reaction of a marking substance in a measurement cycle, the method for indicating comprising:
   a. carrying out the measurement cycle in a calibration process using a liquid sample void of the analyte and performing a first electrochemical impedance spectroscopy, EIS, at a given point of the measurement cycle producing a first EIS result, the first EIS being performed using the working electrode,
   b. carrying out the measurement cycle in an analysis process using a liquid sample containing the analyte and performing a second EIS at the given point of the measurement cycle producing a second EIS result, the second EIS being performed using the working electrode,
   c. comparing the first EIS result and the second EIS result to produce a comparison, and
   d. providing an indication of a measurement state indicating if the comparison results in a deviation between the first EIS result and the second EIS result that exceeds a predefined threshold.

2. The method for indicating of claim 1, the measuring cell being part of a measurement apparatus further comprising a control unit, the indication being provided to the control unit, wherein if the indication indicates that the comparison results in a deviation between the first EIS result and the second EIS result that exceeds the predefined threshold, the method for indicating further comprises controlling by the control unit the measurement apparatus to:
   select a countermeasure regarding the deviation between the first EIS result and the second EIS result,
   initiate the countermeasure, and
   repeat steps b., c. and d.

3. The method for indicating of claim 2, the measurement apparatus further comprising a display unit, the countermeasure comprising displaying the measurement state on the display unit.

4. The method for indicating of claim 3, wherein the given point is one or more of the following:
   a first point during a first phase,
   a second point during a second phase,
   a third point during a third phase,
   a fourth point during a fourth phase, and
   a fifth point after a fifth phase and before the first phase;
   the first phase comprising conditioning of the working electrode without the liquid sample void of the analyte, or without the liquid sample containing the analyte,
   the second phase comprising provisioning of the liquid sample void of the analyte to the measuring cell for the calibration process, or provisioning of the liquid sample containing the analyte to the measuring cell for the analysis process, and capturing of magnetic microparticles, said liquid sample void of the analyte and said liquid sample containing the analyte both comprising a marking substance capable of effecting an electrochemiluminescence reaction measured with an electrochemiluminescence measurement, wherein for the liquid sample containing the analyte, complexes are produced that comprise the analyte and the marking substance, said complexes being bound to the magnetic microparticles, said capturing comprising attracting the magnetic microparticles by a magnetic field thereby depositing the magnetic microparticles on a surface of said working electrode, the third phase comprising washing of the measuring cell after the capturing and before the electrochemiluminescence measurement, said third phase being adapted to remove from the measuring cell marking substance bound to magnetic microparticles which are not yet deposited on the surface of the working electrode, the fourth phase comprising performing the electrochemiluminescence measurement on the liquid sample containing the analyte or the liquid sample void of the analyte, and the fifth phase comprising cleaning of the measuring cell with a cleaning solution.

5. The method for indicating of claim 4, wherein the conditioning, the capturing, the washing, the electrochemiluminescence measurement and the cleaning comprise applying potential pulses to the working electrode, the potential pulses being applied relative to a DC polarization potential measured relative to a reference electrode of the measuring cell, the performing of the first and second EIS comprising applying an AC potential on a DC potential.

6. The method for indicating according to claim 5, wherein the AC potential for performing of the first and second EIS is applied using a potentiostat with a Frequency Response Analysis (FRA) module.

7. The method for indicating according to claim 5, wherein the AC potential has an amplitude of at least 1 mV and at most 100 mV peak to peak.

8. The method for indicating according to claim 5, wherein the AC potential has a frequency of at least 10 Hz and at most 100 kHz.

9. The method for indicating of claim 4, wherein the indication of a measurement state is positive if the comparison results in a deviation between the first EIS result and the second EIS result that is within the predefined threshold, and the indication of a measurement state is negative if the comparison results in a deviation between the first EIS result and the second EIS result that is outside the predefined threshold, the first EIS and second EIS being performed at least twice for at least two different ones of the given point and resulting in an assay run indication of measurement state for each of the at least two different ones of the given point, wherein the selecting of the countermeasure is performed based on a combination of the respective assay run indications of the measurement states.

10. The method for indicating of claim 9, the at least two different ones of the given point comprising the fifth point, the method for indicating further comprising:

carrying out the measurement cycle in a prepare run process using a liquid sample void of any analyte and performing a third EIS at the fifth point producing a third EIS result, the third EIS being performed using the working electrode, comparing the first EIS result produced by the first EIS at the fifth point to the third EIS result, providing a prepare run indication of a measurement state indicating if the comparison results in a deviation between the first EIS result and the third EIS result produced at the fifth point that exceeds a predefined threshold, wherein the selecting of the countermeasure is performed further based on a combination of the respective assay run indications of the measurement states and the prepare run indication.

11. The method for indicating of claim 10 and further including obtaining assay run indications for the first, second and third points, wherein if one of the assay run indications obtained for the first, second and third points is positive, the assay run indication obtained for the fifth point is negative, and the prepare run indication obtained for the fifth point is negative, the selected countermeasure comprises either displaying via the display unit an instruction to replace the cleaning solution with a cleaning solution of a different lot unit, or the selected countermeasure comprises an automated cleaning of components of the measurement apparatus that are used for performing the cleaning of the measuring cell.

12. The method for indicating of claim 10 and further including obtaining assay run indications for the first, second and third points, wherein if one of the assay run indications that has been obtained for the first, second and third points is positive, the assay run indication obtained for the fifth point is negative, and the prepare run indication obtained for the fifth point is positive, the selected countermeasure comprises either displaying via the display unit an instruction to replace the liquid sample containing the analyte with a new liquid sample containing the analyte, or a request for an automated provision of a further liquid sample containing the analyte.

13. The method for indicating of claim 9 and further including obtaining assay run indications for the first, second and third points, further comprising providing a co-reactant solution to the measuring cell which in combination with the complexes results in an electrochemiluminescence reaction of the marking substance, wherein a first determination is made if a criterion is fulfilled in that one of the assay run indications obtained for the first and third points is negative, or an assay run indication obtained for the second point is negative while at least a further assay run indication obtained for the first, third or fifth point is also negative, wherein if it is determined by the first determination that the criterion is fulfilled, the selected countermeasure comprises displaying via the display unit an instruction to clean components of the measurement apparatus that are used for providing the co-reactant solution to the measuring cell, or the selected countermeasure comprises an automated cleaning of the components of the measurement apparatus that are used for providing the co-reactant solution to the measuring cell, wherein after the countermeasure is performed, steps b., c. and d. are repeated, and a second determination is made if the criterion is fulfilled in that an assay run indication obtained for the first or third point is still negative, or an assay run indication obtained for the second point is negative while at least a further assay run indication obtained for the first, third or fifth point is also negative, wherein if it is determined by the second determination that the criterion is fulfilled the selected countermeasure comprises either displaying via the display unit an instruction to clean the measuring cell using an alkaline solution, or the selected countermeasure comprises an automated liquid flow cleaning of the measuring cell using an alkaline solution.

14. The method for indicating of claim 9, wherein if an assay run indication obtained for the first, third or fifth point is positive, an assay run indication obtained for the second point is negative, and the selected countermeasure comprises either displaying via the display unit an instruction to clean components of the measurement apparatus that are used for the provisioning of the liquid sample containing the analyte to the measuring cell, or the selected countermeasure comprises an automated cleaning of components of the measurement apparatus that are used for a provisioning of the liquid sample containing the analyte to the measuring cell and/or a mechanical calibration of the measurement apparatus.

15. The method for indicating of claim 4 in which the given point comprises a point during the fourth phase.

16. The method for indicating of claim 2, the method for indicating further comprising comparing said second EIS result at the given point with a second EIS result obtained for the same given point in an nth-to-the-last preceding run of the measurement cycle, n being a variable in between 1 and 1000, wherein the selected countermeasure is only performed if a comparison of the second EIS result at the given point and the second EIS result obtained for the same given point in the nth-to-the-last preceding run of the measurement cycle results in a deviation exceeding a predefined aging threshold.

17. The method for indicating of claim 1, wherein the first EIS result and the second EIS result each comprises a response signal indicating an admittance and a phase, the predefined threshold being defined as a first threshold for the admittance and a second threshold for the phase, the comparison of the first EIS result and second EIS result comprising a first comparison of the admittance of the first EIS result and the admittance of the second EIS result and a second comparison of the phase of the first EIS result and the phase of the second EIS result, the measurement state indicating if the first comparison results in a deviation between the first EIS result and the second EIS result that exceeds the first threshold, and the measurement state indicating if the second comparison results in a deviation between the first EIS result and the second EIS result that exceeds the second threshold.

\* \* \* \* \*